United States Patent [19]

Ireland et al.

[11] Patent Number: 5,414,001
[45] Date of Patent: May 9, 1995

[54] ANTINEOPLASTIC PYRROLO[4,3,2-DE]QUINOLIN-8(1H)-ONES

[75] Inventors: Chris M. Ireland, Sandy; Derek C. Radisky; Louis R. Barrows, both of Salt Lake City, all of Utah; Robert Kramer, Upper Saddle River, N.J.

[73] Assignee: American Cyanamid Company, Wayne, N.J.

[21] Appl. No.: 48,441

[22] Filed: Apr. 16, 1993

Related U.S. Application Data

[63] Continuation of Ser. No. 890,989, May 29, 1992, abandoned.

[51] Int. Cl.⁶ .................. A61K 31/44; C07D 471/00
[52] U.S. Cl. ................................ 514/287; 514/292; 546/64; 546/84
[58] Field of Search ............. 546/64, 84; 514/287, 514/292

[56] References Cited

PUBLICATIONS

Sun, H. H.; Sakemi, S.; Burres, N.; McCarthy, P. "J. Org. Chem.", 1990, 55, 4964.
Sakemi, S.; Sun, H.; Jefford, C. W.; Bernardinelli, G. "Tetrahedron Lett." 1989, 30, 2517.
Stierle, D. B.; Faulkner, D. J. "J. Nat. Prod.", 1991, 54, 1131.
Kobayashi, J.; Cheng, J.; Ishibashi, M.; Nakamura, H.; Ohizumi, Y.; Hirata, Y.; Sasaki, T.; Lu, H.; Clardy, J. "Tetrahedron Lett." 1987, 28, 4939.
Cheng, J.; Ohizumi, Y.; Walchli, M. R.; Nakamura, H.; Hirata, Y.; Sasaki, T.; Kobayashi, J. "J. Org. Chem." 1988, 53, 4621.
Kobayashi, J.; Cheng, J.; Yamamura, S.; Ishibashi, M. "Tetrahedron Lett." 1991, 32, 1227.
Kobayashi et al, Tetrahedron Letters, 32(9) pp. 1227–1228, 1991.

*Primary Examiner*—Marianne M. Cintins
*Assistant Examiner*—Phyllis G. Spivack

[57] ABSTRACT

The invention discloses certain antitumor pyrrolo[4,3,2-de]quinolin-8(1H)-ones isolated from the Fijian marine sponge *Z. cf. marsailis* and structurally modified compounds thereof and pharmaceutical compositions.

71 Claims, No Drawings

ANTINEOPLASTIC PYRROLO[4,3,2-DE]QUINOLIN-8(1H)-ONES

This is a continuation of application Ser. No. 07/890,989, filed on May, 29, 1992, now abandoned.

BACKGROUND OF THE INVENTION

This invention was made with government support under CA36622 awarded by National Institutes of Health. The government has certain rights in this invention.

FIELD OF THE INVENTION

This invention relates to certain pyrrolo[4,3,2-de]-quinolin-8(1H)-ones which have demonstrated activity as antineoplastic and antibacterial agents and are therefore useful in treating tumors and bacterial infections.

DESCRIPTION OF THE PRIOR ART

The investigation of the chemistry of marine organisms is not new. However, the rationale for investigating the chemistry of marine organisms has changed. Early investigations were largely of a "phytochemical" nature, reporting detailed metabolite profiles. More recent studies of marine organisms have focused on the treatment of human disease. A series of recent publications have described cytotoxic pyrrolo iminoquinones based on a pyrrolo[4,3,2-de]quinoline skeleton. Sun, H. H.; Sakemi, S.; Burres, N.; McCarthy, P. *J. Org. Chem.*, 1990, 55, 4964 and Sakemi, S.; Sun, H. H.; Jefford, C. W.; Bernardinelli, G. *Tetrahedron Lett.* 1989, 30, 2517 describe the batzellines and isobatzellines isolated from the Caribbean sponge Batzella sp.. Stierle, D. B.; Faulkner, D. J., *J. Nat. Prod.*, 1991, 54, 1131 describe damirones isolated from the Palauan sponge Damiria sp.. Kobayashi, J.; Cheng, J.; Ishibashi, M.; Nakamura, H.; Ohizumi, Y.; Hirata, Y.; Sasaki, T.; Lu, H.; Clardy, J. *Tetrahedron Lett.* 1987, 28, 4939. Cheng, J.; Ohizumi, Y.; Walchli, M. R.; Nakamura, H.; Hirata, Y.; Sasaki, T.; Kobayashi, J. *J. Org. Chem.*, 1988, 53, 4621 and Kobayashi, J.; Cheng, J.; Yamamura, S.; Ishibashi, M. *Tetrahedron Lett.* 1991, 32, 1227 describe prianosins isolated from the Okinawan sponge Prianosmelanos.

SUMMARY OF THE INVENTION

The invention is a series of pyrrolo[4,3,2-de]quinolin-8(1H)-ones isolated in substantially pure form from the Fijian marine sponge *Z. cf. marsailis* and structurally modified compounds from the series. The invention includes the use of these compounds as antitumor agents. The invention includes the use of the compounds as antibacterial agents. The invention is also pharmaceutical compositions containing the compounds, method of isolating essentially pure compounds and processes to modify the compounds structurally.

DETAILED DESCRIPTION OF THE INVENTION

The invention is essentially pure and structurally modified novel compounds of Formulae I, II and III, below, which have antineoplastic and cytotoxic activity as well as antibacterial activity. The essentially pure and structurally modified compounds are:

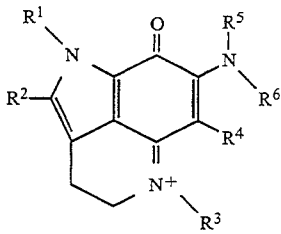

Formula I

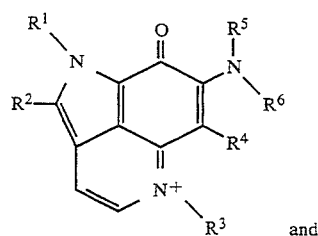

Formula II and

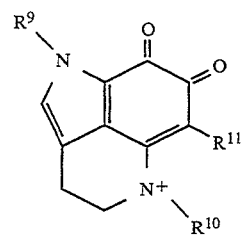

Formula III wherein $R^1$ is H, straight alkyl of 1 to 4 carbon atoms, allyl, benzyl, mono-substituted benzyl (substitution of straight alkyl of 1 to 4 carbon atoms, trifluoromethyl, nitro, O-alkyl of 1 to 4 carbon atoms straight chain, —NR$^7$R$^7$, F, Cl, Br, OH,

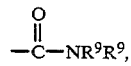

or —CO$_2$R$^9$), di-substituted benzyl (substitution of straight alkyl of 1 to 4 carbon atoms, trifluoromethyl, nitro, 0-alkyl of 1 to 4 carbon atoms straight chain, —NR$^7$R$^7$, F, Cl, Br, OH,

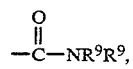

or —CO$_2$R$^9$),

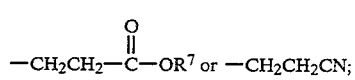

$R^2$ is H, Cl, Br or I;
$R^3$ is H, straight alkyl of 1 to 4 carbon atoms, benzyl, mono-substituted benzyl, (substitution of straight alkyl of 1 to 4 carbon atoms, trifluoromethyl, nitro, or O-alkyl of 1 to 4 carbon atoms straight chain, —NR$^7$R$^7$, F, Cl, Br, OH,

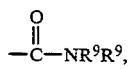

or —CO$_2$R$^2$) di-substituted benzyl (substitution of straight alkyl of 1 to 4 carbon atoms, trifluoromethyl, nitro, O-alkyl of 1 to 4 carbon atoms straight chain, —NR$^7$R$^7$, F, Cl, Br, OH,

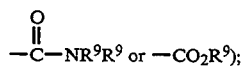

R$^4$ is H, straight alkyl of 1 to 4 carbon atoms, Cl, Br, I, benzyl, mono-substituted benzyl (substitution of straight alkyl of 1 to 4 carbon atoms, trifluoromethyl, nitro or O-alkyl of 1 to 4 carbon atoms straight chain, —NR$^7$R$^7$, F, Cl, Br, OH,

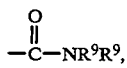

or —CO$_2$R$^9$) di-substituted benzyl (substitution of straight alkyl of 1 to 4 carbon atoms, trifluoromethyl, nitro, O-alkyl of 1 to 4 carbon atoms straight chain, —NR$^7$R$^7$, F, Cl, Br, OH,

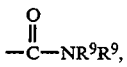

or —CO$_2$R$^9$);

R$^5$ is H, straight or branched alkyl of 1 to 10 carbon atoms,

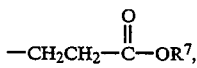

—CH$_2$R$^8$ benzyl mono-substituted benzyl (substitution of straight alkyl of 1 to 4 carbon atoms, trifluoromethyl, nitro, O-alkyl of 1 to 4 carbon atoms, straight chain, hydroxyl, —NR$^7$R$^7$, F, Cl, Br

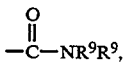

or —CO$_2$R$^9$), disubstituted benzyl (substitution of straight alkyl of 1 to 4 carbon atoms, trifluoromethyl, nitro, O-alkyl of 1 to 4 carbon atoms straight chain, hydroxyl, —NR$^7$R$^7$, F, Cl, Br,

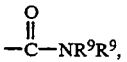

or —CO$_2$R$^9$), —CH$_2$-furan, —CH$_2$-thiophene, —CH$_2$-naphthyl, —CH$_2$-pyridyl

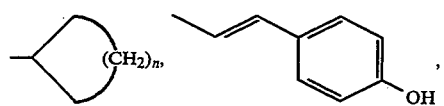

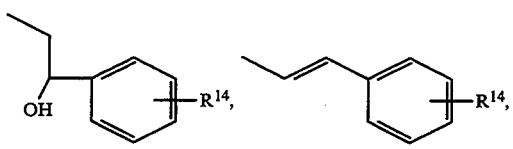

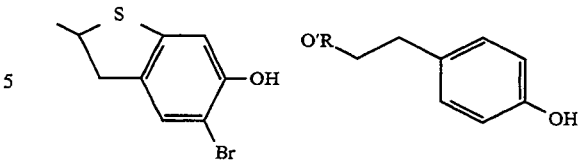

phenyl, mono-substituted phenyl(substitution of straight alkyl of 1 to 4 carbon atoms, trifluoromethyl, nitro, O-alkyl of 1 to 4 carbon atoms straight chain, hydroxyl, F, Cl, or Br), disubstituted phenyl (substitution of straight alkyl of 1 to 4 carbon atoms, trifluoromethyl, nitro, O-alkyl of 1 to 4 carbon atoms straight chain, hydroxyl, F, Cl, or Br);

n is 2 to 5;
R$^6$ is H, or CH$_2$R$^8$;
R$^7$ is straight alkyl 1 to 4 carbon atoms;
R$^8$ is straight alkyl 1 to 7 carbon atoms;
R$^9$ is H or straight alkyl 1 to 4 carbon atoms;
R$^{10}$ is H or straight alkyl 1 to 4 carbon atoms;
R$^{11}$ is H or Br;
R$^{14}$ is F, Cl, Br, NO$_2$, straight alkyl of 1 to 4 carbon atoms, O-alkyl of 1 to 4 carbon atoms straight chain or trifluoromethyl; and pharmaceutically acceptable salts.

Sponge specimens of *Z. cf. marsailis* collected from coastal waters of the Fiji islands (coordinates 18° 11 min south, 178° 32 min. west) on two separate occasions are stored at −20° C. for up to 1 year and treated separately. Methanol extracts of the first collection are subjected to a solvent partition scheme with chloroform, methanol and hexanes. The chloroform soluble material is flash chromatographed on silica gel followed by chromatography with lipophilic sephadex LH-20 to yield the essentially pure compounds according to Formula I, 7-amino-3,4-dihydro-1-methyl-pyrrolo[4,3,2-de]quinolin-8(1H)-one trifluoroacetate (makaluvamine A) 1 where R$^1$ is methyl, R$^2$, R$^3$, R$^4$, R$^5$ and R$^6$ are H, 3,4-dihydro-7-[[2-(4-hydroxyphenyl)ethyl]amino]pyrrolo[4,3,2-de]quinolin-8(1H)-one trifluoroacetate (makaluvamine D) 4 where R$^1$, R$^2$, R$^3$, R$^4$ and R$^5$ are H and R$^6$ is 2-(4-hydroxyphenyl)ethyl, (E)-7-[[2-(4-hydroxyphenyl)ethenyl]amino]-1-methyl-3,4-dihydropyrrolo[4,3,2-de]quinolin-8(1H)-one trifluoroacetate (makaluvamine E) 5 where R$^1$ is methyl and R$^2$, R$^3$, R$^4$ and R$^5$ are H and R$^6$ is [2-(4-hydroxyphenyl)ethenyl]amino, 7-(5-bromo-2,3-dihydro-6-hydroxybenzo[b]thien-2-yl)-3,4-dihydro-pyrrolo[4,3,2-de]quinolin-8(1H)-one trifluoroacetate (makaluvamine F) 6 where R$^1$, R$^2$, R$^3$, R$^4$ and R$^5$ are hydrogen and R$^6$ is 5-bromo-2,3-dihydro-6-hydroxybenzo-[b]thien-2-yl. An essentially pure compound according to Formula II 7-amino-1-methyl-pyrrolo[4,3,2-de]quinolin-8(1H)-one trifluoroacetate (makaluvamine B) 2 where R$^1$ is methyl, R$^2$, R$^3$, R$^4$, R$^5$ and R$^6$ are hydrogen is also obtained. Further elution gives an essentially pure compound according to Formula III 6-bromo-1,3,4,5-tetrahydro-1-methyl-pyrrolo[4,3,2-de]quinoline-7,8-dione (makaluvone) trifluoroacetate 7 where R$^9$ is methyl, R$^{10}$ is hydrogen and R$^{11}$ is bromo.

The second collection of Fijian marine sponge *Z. cf. marsailis* is also subjected to the same solvent partition scheme and chromatography and gives according to Formula I, the essentially pure compounds 7-amino-3,4-dihydro-1-methyl-pyrrolo-[4,3,2-de]quinolin-8(1H)-one trifluoroacetate (makaluvamine A) 1 and 7-amino- 1,3,4,8-tetrahydro-5-methyl-8-oxo-pyrrolo[4,3,2-de]-quinolinium trifluoroacetate 3 (makaluvamine C) where $R^1$, $R^2$, $R^4$, $R^5$ and $R^6$ are hydrogen and $R^3$ is methyl following chromatography on lipophilic sephadex LH-20 and silica gel. The structures of the essentially pure isolated products from natural sources are shown in Table I.

TABLE 1

Isolated Pyrrolo[4,3,2-do]quililnes From Natural Sources

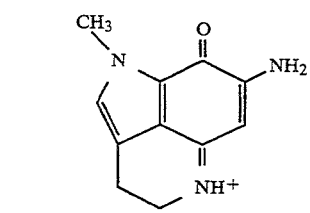  1

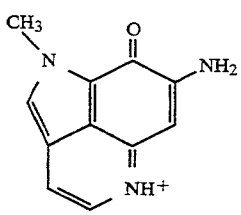  2

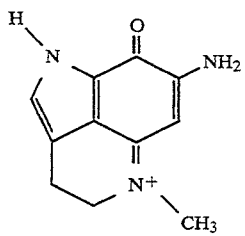  3

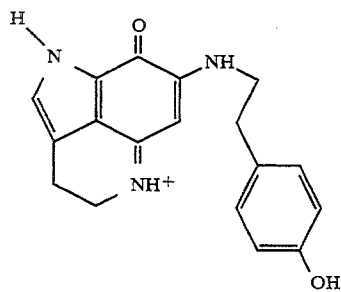  4

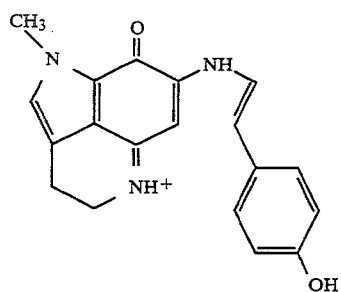  5

TABLE 1-continued

Isolated Pyrrolo[4,3,2-do]quililnes From Natural Sources

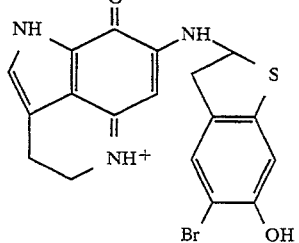  6

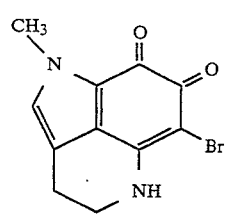  7

The essentially pure isolated compounds are chemically modified according to the following schemes.

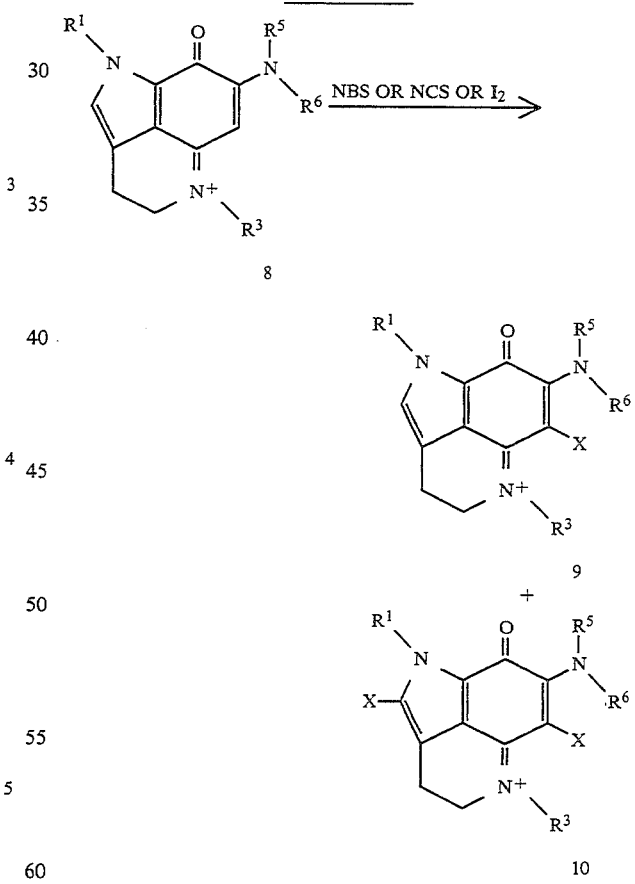

Referring to Scheme I, the corresponding pyrrolo[4,3,2-de]quinoline 8 where $R^1$, $R^3$, $R^5$ and $R^6$ are hereinbefore defined are stirred with N-bromosuccinimide in methyl alcohol to provide where X is bromo, the monobromo compound 9 or a mixture of monobromo compound 9 and the dibromo compound 10. Products 9 and 10 are separated by chromatography.

When the pyrrolo[4,3,2-de]quinoline 8 is stirred with N-chlorosuccinimide in methyl alcohol, the monochloro compound 9, where X is chloro, is isolated. When the pyrrolo[4,3,2-de]quinoline 8 is stirred with iodine in methyl alcohol the monoiodo compound 9, where X is iodo, is obtained.

In Scheme II, the corresponding pyrrolo[4,3,2-de]-quinoline 11 where $R^2$, $R^3$, $R^4$, $R^5$ and $R^6$ are hereinbefore defined are alkylated or benzylated with $R^1Y$ where $R^1$ is straight alkyl of 1 to 4 carbon atoms, allyl, benzyl, mono-substituted benzyl (substitution of straight alkyl of 1 to 4 carbon atoms, trifluoromethyl, nitro, O-alkyl of 1 to 4 carbon atoms straight chain, —$NR^7R^7$, F, Cl, Br, OH,

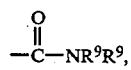

or —$CO_2R^9$), disubstituted benzyl (substitution of straight alkyl of 1 to 4 carbon atoms, trifluoromethyl, nitro, O-alkyl of 1 to 4 carbon atoms straight chain, hydroxyl, —$NR^7R^7$, Cl, Br, OH,

or —$CO_2R^9$) where $R^7$ and $R^9$ are hereinbefore defined and Y is bromo or iodo in the presence of sodium bicarbonate or other suitable base such as diisopropylethylamine,

SCHEME II

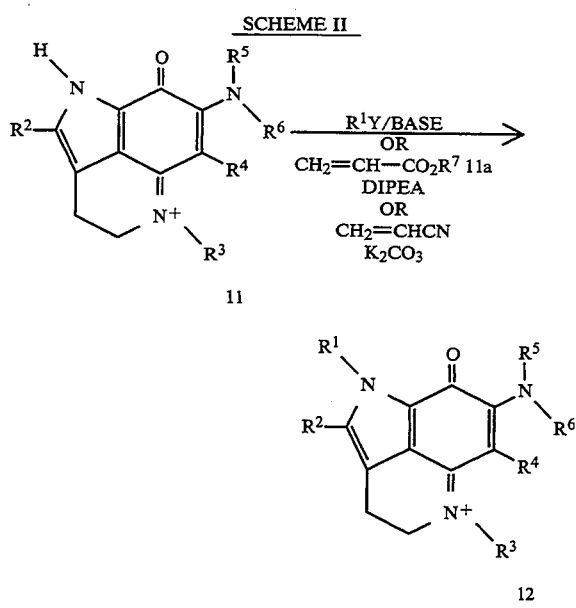

sodium carbonate, cesium carbonate, sodium ethoxide, lithium methoxide, sodium t-butoxide or potassium t-butoxide in an alkanolic solvent such as methanol for 2–24 hours at room temperature to give the alkylated pyrrolo[4,3,2-de]quinolines 12. Additionally, reaction of 11 with acrylates 11a where $R^7$ is hereinbefore defined in the presence of diisopropylethylamine affords 12 where $R^1$ and/or $R^5$ are substituted with

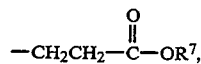

where $R^7$ is hereinbefore defined, or with acrylonitrile in the presence of potassium carbonate to give 12 where $R^1$ is substituted with —$CH_2CH_2CN$.

As shown in Scheme III, pyrrolo[4,3,2-de]quinoline 13 where $R^1$, $R^2$, $R^3$ and $R^4$ are hereinbefore defined are allowed to react with alkyl aldehydes or ketones

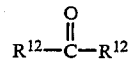

where $R^{12}$ is H or straight or branched alkyl of 1 to 10 carbon atoms, alicyclic ketones

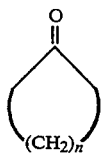

where n is hereinbefore defined, aromatic aldehydes, $R^{13}CHO$ where $R^{13}$ is phenyl, mono-substituted phenyl, (substitution of straight alkyl of 1 to 4 carbon atoms, trifluoromethyl, nitro, O-alkyl of 1 to 4 carbon atoms straight chain, —$NR^7R^7$, F, Cl, Br, OH,

or —$CO_2R^9$), disubstituted phenyl, (substitution of straight alkyl of 1 to 4 carbon atoms, trifluoromethyl, nitro, O-alkyl of 1 to 4 carbon atoms straight chain, —$NR^7R^7$, F, Cl, Br, OH,

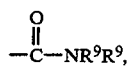

or —$CO_2R^9$) where $R^7$ and $R^9$ are hereinbefore defined, 2-furaldehyde, 3-furaldehyde, 2-thiophenecarboxaldehyde, 3-thiophenecarboxaldehyde, 2-pyridinecarboxaldehyde, 3-pyridinecarboxaldehyde, 4-pyridinecarboxaldehyde, 1-naphthaldehyde, or 2-naphthaldehyde, by reductive alkylation in the presence of $NaBH_4$ or $NaBD_4$ in a preferred solvent methanol to give the desired substituted product 14. In the case where

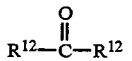

is formaldehyde, the disubstituted product 15 is obtained.

SCHEME III

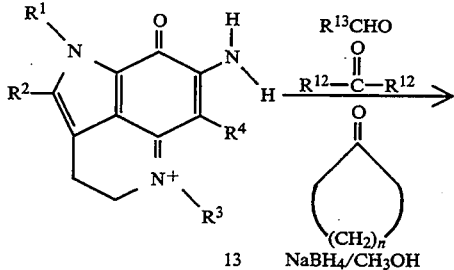

-continued
SCHEME III

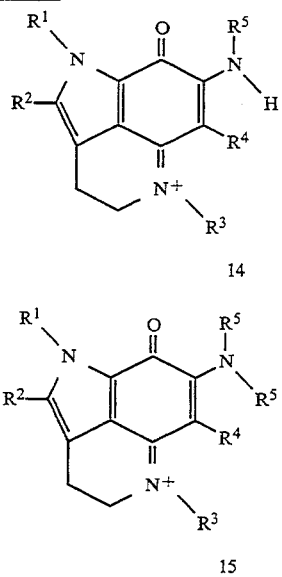

SCHEME IV

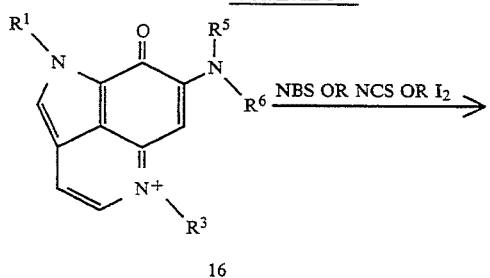

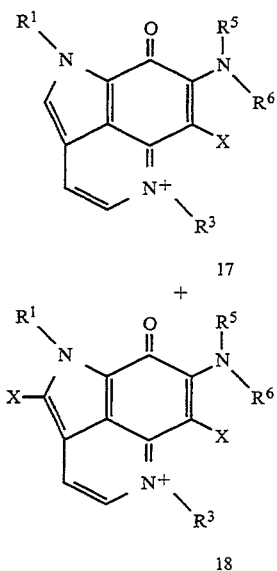

Referring to Scheme IV, the corresponding pyrrolo[4,3,2-de]quinoline 16 where $R^1$, $R^3$, $R^5$ and $R^6$ are hereinbefore defined are stirred with N-bromosuccinimide in methyl alcohol to provide, where X is bromo, the monobromo compound 17 or a mixture of the monobromo compound 17 and the dibromo compound 18. Products 17 and 18 are separated by chromatography. When the pyrrolo[4,3,2-de]quinoline 16 is stirred with N-chlorosuccinimide in methyl alcohol the monochloro compound 17, where X is chloro, is obtained. When the pyrrolo[4,3,2-de]quinoline 16 is stirred with iodine in methyl alcohol the monoiodo compound 17, where X is iodo is obtained.

In Scheme V, the corresponding pyrrolo[4,3,2-de]quinoline 19 where $R^2$, $R^3$, $R^4$, $R^5$ and $R^6$ are hereinbefore defined are alkylated or benzylated with $R^1Y$ where $R^1$ is straight alkyl of 1 to 4 carbon atoms, allyl, benzyl, mono-substituted benzyl (substitution of straight alkyl of 1 to 4 carbon atoms, trifluoromethyl, nitro, O-alkyl of 1 to 4 carbon atoms straight chain, —$NR^7R^7$, F, Cl, Br, OH,

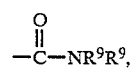

or —$CO_2R^9$), disubstituted benzyl (substitution selected from straight alkyl of 1 to 4 carbon atoms, trifluoromethyl, nitro, O-alkyl of 1 to 4 carbon atoms straight chain, hydroxyl, —$NR^7R^7$, F, Cl, Br, OH,

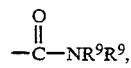

or —CO $R^9$) where $R^7$ and $R^9$ are hereinbefore defined and Y is bromo or iodo in the presence of sodium bicarbonate or other suitable base such as diisopropylethylamine, sodium carbonate, cesium carbonate, sodium ethoxide, lithium methoxide, sodium t-butoxide or potassium t-butoxide in an alkanolic solvent such as methanol for 2–24 hours at room temperature to give the alkylated pyrrolo[4,3,2-de]quinolines 20. Additionally, reaction of 19 with acrylates 11a in the presence of diisopropylethylamine affords 20 where $R^1$ and/or $R^5$ are substituted with

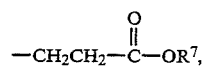

where $R^7$ is hereinbefore defined, or with acrylonitrile in the presence of potassium carbonate to give 20 where $R^1$ is substituted with —$CH_2CH_2CN$.

SCHEME V

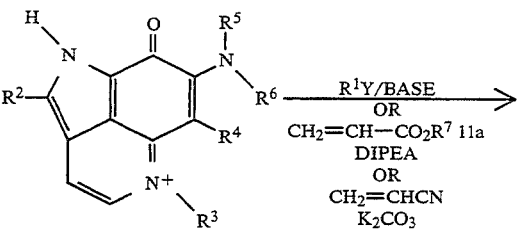

-continued
SCHEME V

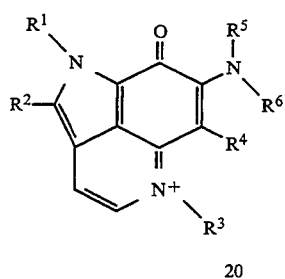

As shown in Scheme VI, pyrrolo[4,3,2-de]quinoline 21 where $R^1$, $R^2$, $R^3$ and $R^4$ are hereinbefore defined are allowed to react with alkyl aldehydes or ketones

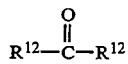

where $R^{12}$ is H or straight or branched alkyl of 1 to 10 carbon atoms, alicyclic ketones

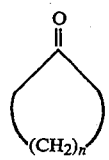

where n is hereinbefore defined, aromatic aldehydes, $R^{13}CHO$ where $R^{13}$ is phenyl, mono-substituted phenyl (substitution selected from straight alkyl of 1 to 4 carbon atoms, trifluoromethyl, nitro, O-alkyl of 1 to 4 carbon atoms straight chain, $-NR^7R^7$, F, Cl, Br, OH,

or $-CO_2R^9$), disubstituted phenyl (substitution selected from straight alkyl of 1 to 4 carbon atoms, trifluoromethyl, nitro, O-alkyl of 1 to 4 carbon atoms straight chain, $-NR^7R^7$, F, Cl, Br, OH,

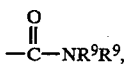

or $-CO_2R^9$) where $R^7$ and $R^9$ are hereinbefore defined, 2-furaldehyde, 3-furaldehyde, 2-thiophenecarboxaldehyde, 3-thiophenecarboxaldehyde, 2-pyridinecarboxaldehyde, 3-pyridinecarboxaldehyde, 4-pyridinecarboxaldehyde, 1-naphthaldehyde, or 2-naphthaldehyde, by reductive alkylation in the presence of $NaBH_4$ or $NaBD_4$ in a preferred solvent methanol to give the desired substituted product 22. In the case where

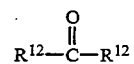

is formaldehyde, the disubstituted product 23 is obtained.

SCHEME VI

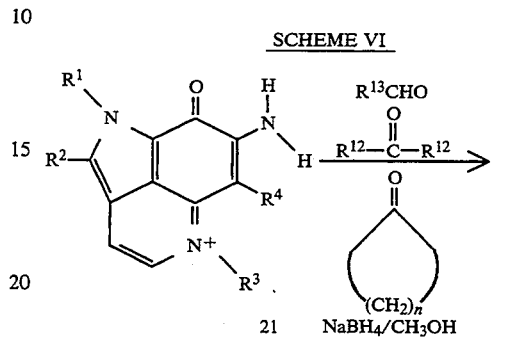

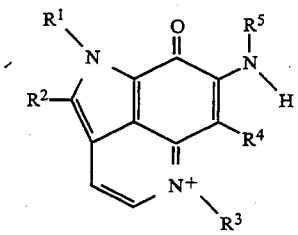

+

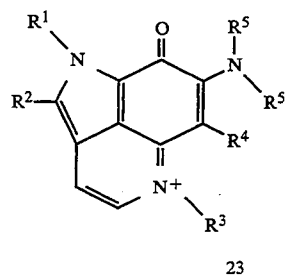

According to Scheme VII, pyrrolo[4,3,2-de]quinoline 26 where $R^1$, $R^2$ and $R^3$ are hereinbefore defined are allowed to react with diones 27 where $R^{17}$ is straight alkyl of 1 to 7 carbon atoms, phenyl, mono-substituted phenyl (substitution of straight alkyl of 1 to 4 carbon atoms, trifluoromethyl, nitro, O-alkyl of 1 to 4 carbon atoms straight chain, hydroxyl, F, Cl, or Br), disubstituted phenyl (substitution of straight alkyl of 1 to 4 carbon atoms, trifluoromethyl, nitro, O-alkyl of 1 to 4 carbon atoms straight chain, hydroxyl, F, Cl, or Br), benzyl or indole in the presence of $NaBH_4$, to give a mixture of quinolinium 28 and symmetrical quinolinium 29. Additionally, 26 is allowed to react with diones 30 where $R^{17}$ is hereinbefore defined and m is 1, 2 or 3 to give the symmetrical quinolinium 31.

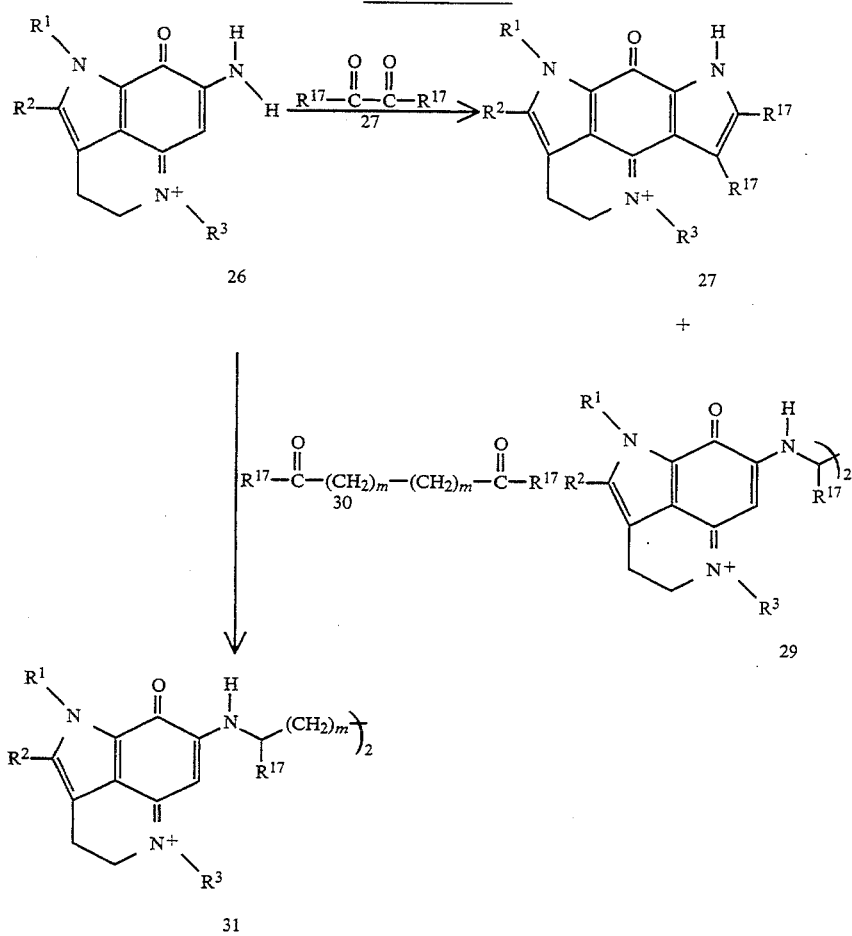
Referring to Scheme VIII, pyrrolo[4,3,2-de]quinoline 13 where $R^1$, $R^2$, $R^3$ and $R^4$ are hereinbefore defined are allowed to react with substituted-phenylglyoxals 32 where $R^{14}$ is hereinbefore defined to give alcohols 33. Dehydration of 33 with trifluoroacetic anhydride gives enamine 34.
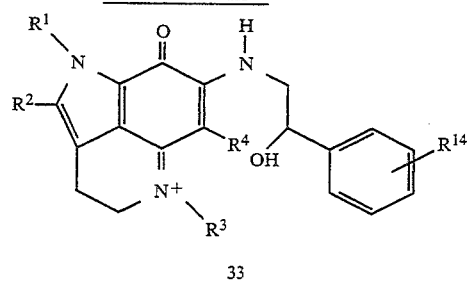
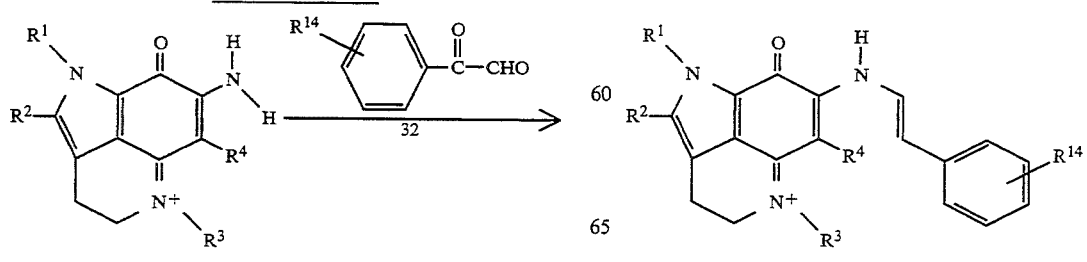

SCHEME IX

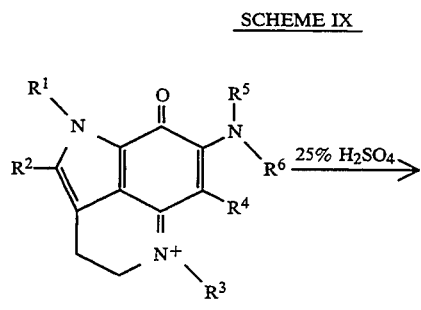

SCHEME X

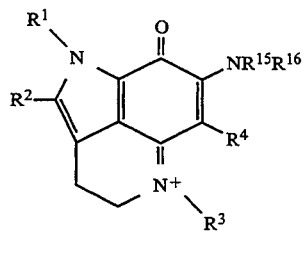

-continued
SCHEME X

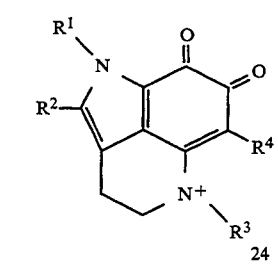

Referring to Scheme IX, pyrrolo[4,3,2-de]quinolines 12 are stirred with 25% sulfuric acid at room temperature to give the pyrrolo[4,3,2-de]quinoline-7,8-diones 24. Additionally, 24 is converted to 35 by reaction with amines 36 wherein $R^{15}$ is H, straight or branched alkyl of 1 to 10 carbon atoms, phenyl, mono-substituted phenyl (substitution of straight alkyl of 1 to 4 carbon atoms, trifluoromethyl, nitro, O-alkyl of 1 to 4 carbon atoms straight chain, hydroxyl, F, Cl, or Br), disubstituted phenyl (substitution of straight alkyl of 1 to 4 carbon atoms, trifluoromethyl, nitro, O-alkyl of 1 to 4 carbon atoms straight chain, hydroxyl, F, Cl or Br), $$-CH_2CH_2-\overset{O}{\underset{\|}{C}}-OR^7,$$

$-CH_2R^8$, benzyl mono-substituted benzyl (substitution of straight alkyl of 1 to 4 carbon atoms, trifluoromethyl, nitro, O-alkyl of 1 to 4 carbon atoms, straight chain, hydroxyl, $-NR^7R^7$, F, Cl, Br $$-\overset{O}{\underset{\|}{C}}-NR^9R^9,$$

or $-CO_2R^9$), disubstituted benzyl (substitution of straight alkyl of 1 to 4 carbon atoms, trifluoromethyl, nitro, O-alkyl of 1 to 4 carbon atoms straight chain, hydroxyl, $-NR^7R^7$, F, Cl, Br, $$-\overset{O}{\underset{\|}{C}}-NR^9R^9,$$

or $-CO_2R^9$), $-CH_2$-furan, $-CH_2$-thiophene, $-CH_2$-naphthyl, $-CH_2$-pyridyl

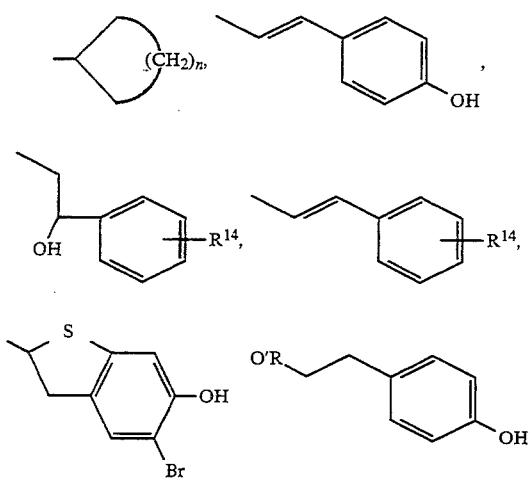

$R^{16}CH_2R^8$.

As shown in Scheme X, pyrrolo[4,3,2-de]quinolines 11 are stirred with 25% sulfuric acid at room temperature to give the pyrrolo[4,3,2-de]quinoline-7,8-diones 25. Additionally, 25 is converted to 37 by reaction with amines 36 wherein $R^{15}$ is H, straight or branched alkyl of 1 to 10 carbon atoms, phenyl, mono-substituted phenyl (substitution of straight alkyl of 1 to 4 carbon atoms, trifluoromethyl, nitro, O-alkyl of 1 to 4 carbon atoms straight chain, hydroxyl, F, Cl, or Br), disubstituted phenyl (substitution of straight alkyl of 1 to 4 carbon atoms, trifluoromethyl, nitro, O-alkyl of 1 to 4 carbon atoms straight chain, hydroxyl, F, Cl or Br),

—$CH_2R^8$, benzyl mono-substituted benzyl (substitution of straight alkyl of 1 to 4 carbon atoms, trifluoromethyl, nitro, O-alkyl of 1 to 4 carbon atoms, straight chain, hydroxyl, —$NR^7R^7$, F, Cl, Br

or —$CO_2R^9$), disubstituted benzyl (substitution of straight alkyl of 1 to 4 carbon atoms, trifluoromethyl, nitro, O-alkyl of 1 to 4 carbon atoms straight chain, hydroxyl, —$NR^7R^7$, F, Cl, Br,

or —$CO_2R^9$), —$CH_2$-furan, —$CH_2$-thiophene, —$CH_2$-naphthyl, —$CH_2$-pyridyl

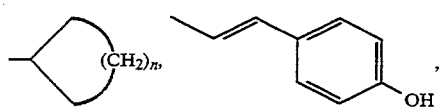

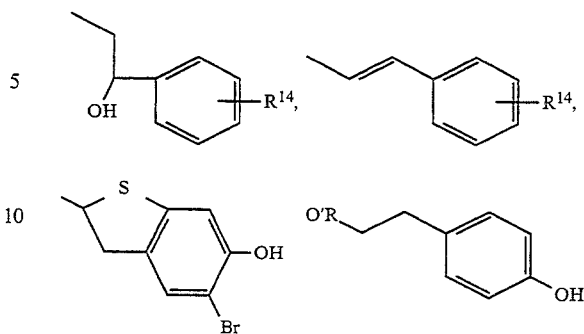

$R^{16}$ is H or $CH_2R^8$.

The reactions are performed in a solvent appropriate to the reagents and materials employed and suitable for the transformation being effected. It is understood by those skilled in the art of organic synthesis that the various functionalities present on the molecule must be consistent with the chemical transformations proposed. This will frequently necessitate judgement as to the order of synthetic steps, protecting groups, if required, and deprotection conditions. substituents on the starting materials may be incompatible with some of the reaction conditions. Such restrictions to the substituents which are compatible with the reaction conditions will be apparent to one skilled in the art.

Pharmaceutically suitable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hygroscopicity and solubility. Preferred salts of this invention for the reasons cited above include sulfate, hydrochloride, hydrobromide and trifluoroacetate.

The compounds of this invention and their preparation can be understood further by the following examples but should not constitute a limitation thereof.

EXAMPLE 1–EXAMPLE 9

Extraction and Isolation Procedures

Specimens of *Z. cf. marsailis* collected at Makaluva Island in November 1986, and at Mbengga harbor in November 1990, both in the Fiji island group are used. The methanol extract of 72.5 g freeze dried sample of the initial collection of sponge material is concentrated in vacuo to a volume of 500 ml and partitioned according to Kupchan, S. M.; Britton, R. W., Ziegler, M. F.; Siegel, C. W., J. Org. Chem., 1973, 38, 178. Briefly, a 10% aqueous methanol solution is partitioned with hexane (3×500 ml). The aqueous content of the lower phase is then increased to 20% and partitioned with carbon tetrachloride (3×500 ml). The aqueous content of the lower phase is further increased to 40% and partitioned with chloroform (3×500 ml), which is concentrated in vacuo to yield 1.02 g (1.41%) of a crude solid. Vacuum flash chromatography (60 ml sintered glass funnel; 20 g silica gel G; step gradient elution from 0 to 10% methanol/chloroform), carried out on 468 mg portion of the chloroform-soluble residue yields a fraction (150 mg, eluting with 7.5% methanol/chloroform/0.1% TFA). Further silica gel chromatography using methanol/chloroform mixtures followed by repeated chromatography with LH-20 lipophilic sephadex gel (0.1% TFA/methanol or 50% methanol/-chloroform/0.1% TFA) yields 80 mg of 7-amino-3,4-dihydro-1-methyl-pyrrolo[4,3,2-de]quinolin-8(1H)-one trifluoroacetate (makaluvamine A) (Example 1), 18 mg of 7-amino-1-methyl-pyrrolo-[4,3,2-de]quinolin-8(1H)-one trifluoroacetate (makaluvamine B) (Example 2), 4 mg of 7-[[2-(4-hydroxyphenyl)ethyl]amino]-3,4-dihydropyrrolo[4,3,2-de]quinolin-8(1H)-one trifluoroacetate (makaluvamine D) (Example 4), 6 mg of (E)-7-[[2-(4hydroxyphenyl)ethenyl]amino]-1-methyl-3,4-dihydropyrrolo[4,3,2-de]-quinolin-8(1H)-one trifluoroacetate (makaluvamine E) (Example 5), 10 mg of 7-(5-bromo-2,3-dihydro-6-hydroxybenzo[b]-thien-2-yl)-3,4-dihydropyrrolo-[4,3,2-de]quinolin-S(1H)-one trifluoroacetate (makaluvamine F) (Example 6), 6 mg of 6-bromo-1,3,4,5-tetrahydro-1-methyl-pyrrolo[4,3,2-de]-quinoline-7,8dione (makaluvone) trifluoroacetate (Example 7).

The methanol extract of 315 g of freeze dried sample of the second collection of Z. cf. marsailis sponge is extracted and solvent-partitioned similarly, yielding 45.8 mg of 7-amino-3,4-dihydro-1-methyl-pyrrolo[4,3,2-de]quinolin-8(1H)-one trifluoroacetate (makaluvamine A) (Example 1), 187.9 mg of 7-amino-1,3,4,8-tetrahydro-5-methyl-8-oxo-pyrrolo[4,3,2-de]quinolinium trifluoroacetate (makaluvamine C) (Example 3).

7-amino-3,4-dihydro-1-methyl-pyrrolo [4,3,2-de]-quinolin-8(1H)-one trifluoroacetate (makaluvamine A) (Example 1) green solid; 80 mg (0.24% dry weight); IR (TFA salt) $\nu_{max}$ 3231, 3042, 2930, 1674, 1606, 1203, 1130, 840, 719 cm$^{-1}$; UV (MeOH): $\Xi_{max}$ 242.2 ($\xi$ 24000), 348.4 mn (15500); (MeOH+OH; irreversible over time) 219.7 ($\xi$ 17400), 330.1 nm (16100); HR FAB MS m/z=202.0978 (M+H)$^+$, C$_{11}$H$_{12}$N$_3$O requires 202.0980.

7-amino-1-methyl-pyrrolo[4,3,2-de ]quinolin-8 (1H) -one trifluoroacetate (makaluvamine B) (Example 2): red solid; 18 mg (0.05% dry weight); IR (TFA salt) $\nu_{max}$ 3319, 1650, 1573, 1494, 1409, 1326, 1195, 1050, 962, 947, 826, 793 cm$^{-1}$; UV (MeOH): $\Xi_{max}$ 228.0 ($\xi$ 9600), 441.7 nm (4800); (MeOH+OH$^-$) 203.9 ($\xi$ 17200), 419.2 nm (4800); HR FAB MS m/z=200 0827 (M+H)$^+$, C$_{11}$H$_{12}$N$_3$O requires 200.0824.

7-amino-1,3,4,8-tetrahydro-5-methyl-8-oxo-pyrrolo [4,3,2-de]quinolinium trifluoroacetate (makaluvamine C) (Example 3): green solid; 187.9 mg (0.7% dry weight); IR (TFA salt) $\nu_{max}$ 3850, 3741, 3063, 1741, 1671, 1646, 1606, 1516, 1415, 1338, 1296, 1193, 1132, 1036, 961, 916, 793, 721 cm$^{-1}$; UV (MeOH): $\Xi_{max}$ 241.4 ($\xi$ 25300), 357.5 nm (19100); (MeOH+OH$^-$) 246.3 (($\xi$ 20400), 355.1 nm (16900); HR FAB MS m/z=202 0979 (M+H)$^+$, C$_{11}$H$_{12}$N$_3$O requires 202.0980.

7-[[2-(4-hydroxyphenyl)ethyl]amino]-3,4-dihydro-pyrrolo[4,3,2-de]quinolin-8(1H) -one trifluoroacetate (makaluvamine D) (Example 4): brown solid; 4 mg (0.02% dry weight); IR (TFA salt) $\nu_{max}$ 3342, 2927, 2854, 1643, 1680, 1632, 1555, 1515, 1402, 1203, 1136, 1038, 1027, 835, 801, 757, 722 cm$^{-1}$; UV (MeOH): $\Xi_{max}$ 244.7 ($\xi$ 22000), 347.5 nm (10600); (MeOH+OH$^-$, irreversible over time) 243.0 ($\xi$ 16800), 339.2 nm (12100); HR FAB MS m/z=308 14075 (M+H)$^+$, C$_{18}$H$_{18}$N$_3$O$_2$ requires 308.13990.

(E) -7- [[2-(4-hydroxyphenyl) ethenyl]amino]-1-methyl-3,4-dihydro-pyrrolo[4,3,2-de]quinolin-8 (1H) -one trifluoroacetate (makaluvamine E) (Example 5): green solid; 6 mg (0.02% dry weight); IR(TFA salt) $\nu_{max}$ 3730, 1681, 1650, 1540, 1511, 1454, 1207, 1130, 926, 843, 800, 722, 670 cm$^{-1}$; UV (MeOH): $\Xi_{max}$ 226.4 ($\xi$ 6200), 278.0 (8700), 333.4 (6800), 448.3 (4900), 625.9 nm (5700); (MeOH+OH$^-$, irreversible over time) 313.9 ($\xi$ 8600), 606.7 nm (5000); HR CI MS m/z=320.1384 (M+H)$^+$, C$_{19}$H$_{18}$N$_3$O$_2$ requires 320.1399.

7-(5-bromo-2,3-dihydro-6-hydroxybenzo[b]-thien-2-yl)-3,4-dihydro-pyrrolo[4,3,2-de]quinolin-8(1H) -one trifluoroacetate (makaluvamine F) (Example 6): orange solid; 10 mg (0.03% dry weight); IR (TFA salt) $\nu_{max}$ 3600–2800, 1681, 1633, 1537, 1485, 1433, 1396, 1337, 1318, 1256, 1203, 1134, 1026, 833, 803, 752, 720, 668 cm$^{-1}$; [$\alpha$]$_D$=475.80° (c 0.0248, CH$_3$OH); UV (MeOH): $\Xi_{max}$ 246.3 ($\xi$ 30200), 310.5 (10800), 344.2 nm (14100); (MeOH +OH$^-$), irreversible over time) 324.2 nm ($\xi$ 17700), HR FAB MS m/z=416 0068 (M+H)$^+$, C$_{18}$H$_{15}$$^{79}$BrN$_3$O$_2$S requires 416.0069.

6-bromo-1,3,4,5-tetrahydro-1-methyl-pyrrolo [4,3,2-de]quinoline-7,8-dione trifluoroacetate (makaluvone) (Example 7): grey solid; 10 mg (0.02% dry weight); IR (TFA salt) $\nu_{max}$ 3728, 3263, 1681, 1597, 1555, 1535, 1451, 1394, 1207, 1333, 1054, 1028, 841, 801, 765, 722, 670 cm$^{-1}$; UV (MeOH): $\Xi_{max}$ 246.3 ($\xi$ 10100), 330.1 nm (5500); (MeOH+OH$^-$) 246.4 ($\xi$ 9800), 330.1 nm (6300); HR EI MS m/z=279.9856 (M+) (C$_{11}$H$_9$$^{79}$BrN$_2$O$_2$ requires 279.9848), 281.9839 (C$_{11}$H$_9$$^{81}$BrN$_2$O$_2$ requires 281.9848), 251.9934 (C$_{10}$H$_9$$^{79}$BrN$_2$O requires 251.9899), 253.9892 (C$_{10}$H$_9$$^{81}$BrN$_2$O requires 253.9899).

In addition to Examples 1–7, the previously reported damirone B (Example 8) and discorhabdin A (Example 9) are also isolated. (damirone B): (Example 8) red solid; 20 mg (0.2% dry weight); IR (TFA salt) $\nu_{max}$ 3421, 3118, 2923, 1667, 1584, 1538, 1419, 1323, 1248, 1199, 1116, 1051, 955, 922, 821, 798, 760, 723 cm$^{-1}$; UV(-MeOH): $\Xi_{max}$ 242.1 ($\xi$ 29500), 346.7 nm (19500); (MeOH+OH$^-$) 242.2 ($\xi$ 29000), 347.5 nm (19300); HR FAB MS m/z=203.0820 (M+H)$^+$+(C$_{11}$H$_{11}$N$_2$O$_2$O$_2$ requires 203.0821); (discorhabdin A) (Example 9): green solid; 12 mg (0.04% dry weight).

EXAMPLE 10

7-Amino-6-chloro-1,3,4,8-tetrahydro-5-methyl-8-oxo-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 5 ml of methyl alcohol is treated with 8.5 mg of N-chlorosuccinimide and stirred overnight. Chromatography on LH-20 lipophilic sephadex gel in methyl alcohol/0.1% TFA followed by silica gel flash (15% MeOH/85% CHCl$_3$/0.1% TFA) gives 4.7 mg of the desired product.

$^1$H NMR: 13.189 (s, 1H, NH-1), 9.196 (s, 1H, NH-9), 9.153(s, 1H, NH-9), 7.333 (br d, j=3 Hz, 1H, CH-2), 4.021(t, j=7.5, 2H, CH$_2$-4), 3.812(s, 3H, N(Me)-5), 2.895(t, ju=7.5, 2H, CH$_2$-3), $^{13}$C NMR: 164.820, 158.119, 154.112, 152.112, 152.546, 126.761, 123.107, 122.888, 119.695, 57.344, 43.540, 18.483 HR FAB MS m/z=236.0584 (M+H)$^+$, C$_{11}$H$_{11}$ClN$_3$O requires 236.0591.

EXAMPLE 11

7-Amino-6-chloro-3,4-dihydro-1-methyl-8-oxo-pyrrolo [4,3,2-de]quinolin-8(1H)-one trifluoroacetate A solution of 10 mg of 7-amino-3,4-dihydro-1-methyl-pyrrolo[4,3,2-de]quinolin-8(1H)-one trifluoroacetate (makaluvamine A) in 5 ml of methyl alcohol is treated with 8.5 mg of N-chlorosuccinimide and stirred overnight. Chromatography on LH-20 lipophilic sephadex gel in methyl alcohol/0.1% TFA followed by silica gel flash (15% MeOH/85% CHCl₃/0.1% TFA) gives 3.0 mg of the desired product.

EXAMPLE 12 AND EXAMPLE 13

7-Amino-6-bromo-1,3,4,8-tetrahydro-5-methyl-8-oxo-pyrrolo[4,3,2-de]quinolinium trifluoroacetate and 7-Amino-2,6-dibromo-1,3,4,8-tetrahydro-5-methyl-8-oxo-pyrrolo[4,3,2-de]quinolinium trifluoroacetate A solution of 20 mg of 7-amino-1,3,4,8-tetrahydro-5-methyl-8-oxo-pyrrolo[4,3,2-de]quinolinium trifluoroacetate (makaluvamine C) in 5 ml of methyl alcohol is treated with 22.6 mg of N-bromosuccinimide and stirred overnight. Chromatography on LH-20 lipophilic sephadex gel in methyl alcohol/0.1% TFA followed by silica gel flash (15% MeOH/85% CHCl₃/0.1% TFA) gives 16.4 mg of the first product.

¹H NMR: 13,237(s, 1H, NH-1), 9.194(s, 2H, NH₂-9), 7.334(s, 1H, CH-2), 4.027(t, j=7.5, 2H, CH₂-4), 3.816(s, 3H, N(Me)-5), 2.899(t, j=7.5, 2H, CH₂-3). and 7.5 mg of the second product ¹H NMR: 14.2(br s, 1H, NH-1), 9.315(s, 2H, NH-9), 4.051(t, j=7.5, 2H, CH₂-4), 3.811(s, 3H, N(Me)-5), 2.803(t, j=7.5, 2H, CH₂-3).

EXAMPLE 14 AND EXAMPLE 15

7-Amino-6-bromo-3,4-dihydro-1-methyl-8-oxo-pyrrolo[4,3,2-de]quinolin-8 (1H) -one trifluoroacetate and 7-Amino-2,6-dibromo-3,4-dihydro-1-methyl-pyrrolo[4,3,2-de]quinolin-8 (1H) -one trifluoroacetate A solution of 10 mg of 7-amino-3,4-dihydro-1-methyl-pyrrolo[4,3,2-de]quinolin-8(1H)-one trifluoroacetate (makaluvamine A) in 5 ml of methyl alcohol is treated with 11.3 mg of N-bromosuccinimide and stirred overnight. Chromatography on LH-20 lipophilic sephadex gel in methyl alcohol/0.1% TFA followed by silica gel flash (15% MeOH/85% CHCl₃/0.1% TFA) gives 2.0 mg of the first product.

¹H NMR: 10.21(s, 1H, NH-5), 9.13(s, 1H, NH-9), 8.95(s, 1H, NH-9), 7.39(s, 1H, CH-2), 3.91(s, 3H, N(Me)-1), 3.81(t, j=7.5, 2H, CH₂-4), 2.86(t, j=7.5, 2H, CH₂-3) HR FAB MS m/z=280.0085 (M+H)⁺, C₁₁H₁₁BrN₃O requires 280.0086. and 3.6 mg of the second product ¹H NMR: 10.31(s, 1H, NH-5), 9.28(s, 1H, NH-9), 9.08(s, 1H, NH-9), 3.86(s, 3H, N(Me)-I), 3.86(t, j=7.5, 2H, CH₂-4), 2.81(t, j=7.5, 2H, CH₂-3) HR FAB MS m/z=357.9196 (M+H)⁺, C₁₁H10Br2N₃O requires 357.9191.

EXAMPLE 16

7-Amino-1,3,4,8-tetrahydro-6-iodo-5-methyl-8-oxo-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 5 ml of methyl alcohol is treated with 16 mg of iodine and stirred overnight. Chromatography on LH-20 lipophilic sephadex gel in methyl alcohol/0.1% TFA followed by silica gel flash (15% MeOH/85% CHCl₃/0.1% TFA) gives 1.1 mg of the desired product.

¹H NMR: 13,199(s, 1H, NH-1), 9.206(s, 1H, NH-9), 9.163(s, 1H, NH-9), 7.334(br d, j=2 Hz, 1H, CH-2), 4.024(t, j=7.5, 2H, CH₂-4), 3.815(s, 3H, N(Me)-5), 2.897(t, j=7.5, 2H, CH₂-3).

EXAMPLE 17

7-Amino-1,3,4,8-tetrahydro-5-methyl-8-oxo,1-(2-propenyl)-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 5 ml of methyl alcohol is combined with 15 ul of allyl iodide and 25 mg of sodium bicarbonate and stirred overnight. Chromatography on LH-20 lipophilic sephadex in methyl alcohol/0.1% TFA followed by silica gel flash (15% MeOH/85% CHCl₃/0.1% TFA) gives 7.4 mg of the desired product.

¹H NMR: 9,370(s, 1H, NH-9), 8,641(s, 1H, NH-9), 7.357(s, 1H, CH-2), 6.00(br m, 1H, N(CH₂CHCH₂)-1), 5.683(s, 1H, CH-6), 5.203(d, j=10.5 Hz, 1H, N(CH₂CHC(H$_{cis}$) (H$_{trans}$))-1), 5.094(d, j=17 Hz, 1H, N(CH₂CHC(H$_{cis}$) (H$_{trans}$))-1), 4.877 (d, j=6 Hz, 2H, N(CH₂CHCH₂)-1,3,897(t, j=7.5, 2H, CH₂-4), 3.316(s, 3H, N(Me)-5), 2.919(t, j-7.5, 2H, CH₂-3). HR FAB MS m/z=242.1282 (M+H)⁺, C₁₄H₁₆N₃O requires 242.1293.

EXAMPLE 18

4-Nitrobenzyl bromide

A solution of 200 mg of 3-methoxybenzyl alcohol in 2.5 ml of dry tetrahydrofuran is cooled to 0° C. and 120 ul of PBr₃ added. The reaction is stirred for three hours, extracted with ether and washed with sodium bicarbonate. The organic layer is evaporated to afford the desired product.

EXAMPLE 19

7-Amino-1,3,4,8-tetrahydro-5-methyl-1-[(4-nitrophenyl)methyl]-8-oxo-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 5 ml of methyl alcohol is combined with 27.4 mg of 4-nitrobenzyl bromide and 25 mg of sodium bicarbonate and stirred overnight. Chromatography on LH-20 lipophilic sephadex in methyl alcohol/0.1% TFA followed by silica gel flash (15% MeOH/85% CHCl₃/0.1% TFA) gives 2.5 mg of the desired product.

¹H NMR: 9.338(s, 1H, NH-9), 8.635(s, 1H, NH-9), 8.216(d, j=9.5 Hz, 2H, N(CH₂C₆H₄NO₂)-1), 7.563(s, 1H, CH-2), 7.535(d, j=9.5 Hz, 2H, N(CH₂C₆H₄NO₂)-1, 5.680(s, 2H, N(CH₂C₆H₄NO₂)-1), 5.613(s, 1H, CH-6), 3.909(t,j=7.5, 2H, CH₂-4), 3.3186(s, 3H, N(Me)-5), 2.947(t, j=7.5, 2H, CH₂-3). HR FAB MS m/z=322.1547 (M+H)⁺, C₁₉H₂₀N₃O₂ requires 322.1556.

EXAMPLE 20

3-Chlorobenzyl bromide

A solution of 260 ul of 3-chlorobenzyl alcohol dissolved in 2.5 ml of dry tetrahydrofuran is cooled to 0° C. and 120 ul of PBr₃ added. The reaction is stirred for 3 hours and extracted with ether. The organic layer is washed with saturated sodium bicarbonate and evaporated to give the desired product.

EXAMPLE 21

7-Amino-1-[(3-chlorophenyl]methyl]-1,3,4,8-tetrahydro-5-methyl-8-oxo-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 5 ml of methyl alcohol is combined with 26.3 mg of 3-chlorobenzyl bromide and 25 mg of sodium bicarbonate and stirred overnight. Chromatography on LH-20 lipophilic sephadex in methyl alcohol/0.1 TFA followed by silica gel flash (15% MeOH/85% CHCl$_3$/0.1% TFA) gives 10.1 mg of the desired product.

$^1$H NMR: 9.330(s, 1H, NH-9), 8.666(s, 1H, NH-9), 7.543(s, 1H, CH-2), 7.23–7.40(m, 5H, N(CH$_2$C$_6$H$_4$Cl)-1), 5.674(s, 1H, CH-6), 5.458(s, 2H, N(CH$_2$C$_6$H$_4$Cl)-1), 3.895(t, j=7.5, 2H, CH$_2$-4), 3.586(s, 3H, N(Me)-5), 2.928(t, j=7.5, 2H, CH$_2$-3). HR FAB MS m/z=326.1057 (M+H)$^+$, C$_{18}$H$_{17}$ClN$_3$O requires 326.1060.

EXAMPLE 22

3-Methoxybenzyl bromide

A solution of 270 ul of 3-methoxybenzyl alcohol in 2.5 ml of dry tetrahydrofuran is cooled to 0° C. and 120 ul PBr$_3$ added, followed by stirring for three hours. The reaction mixture is extracted with ether and the organic layer washed with saturated sodium bicarbonate and evaporated to give the desired product.

EXAMPLE 23

7-Amino-1,3,4,8-tetrahydro-1-[(3-methoxyphenyl)methyl]-5-methyl-8-oxo-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 5 ml of methyl alcohol is combined with 19.9 mg of 3-methoxybenzyl bromide and 25 mg of sodium bicarbonate and stirred overnight. Chromatography on LH-20 lipophilic sephadex in methyl alcohol/0.1% TFA followed by silica gel flash (15% MeOH/85% CHCl$_3$/0.1% TFA) gives 4.1 mg of the desired product.

$^1$H NMR: 9.329(s, 1H, NH-9), 8.653(s, 1H, NH-9), 7.514(s, 1H, CH-2), 6.8–7.3(m, 5H, N(CH$_2$C$_6$H$_4$OCH$_3$)-1), 5.675(s, 1H, CH-6), 5.419(s, 2H, N(CH$_2$C$_6$H$_4$OCH$_3$)-1), 3.890(t, j=7.0, 2H, CH$_2$-4), 3.722(s, 3H, N(CH$_2$C$_6$H$_4$OCH$_3$)-1), 3.306(s, 3H, N(Me)-5), 2.928(t, j=7 0, 2H, CH$_2$-3) HR FAB MS m/z=322.1547 (M+H)$^+$, C$_{19}$H$_{20}$N$_3$O$_2$ requires 322.1556.

EXAMPLE 24

7-Amino-1,3,4,8-tetrahydro-5-methyl-8-oxo-1-(phenylmethyl)pyrrolo[4,3,2-de]quinolinium trifluoroacetate A solution of 25 mg of 7-amino-1,3,4,8-tetrahydro-5-methyl-8-oxo-pyrrolo[4,3,2-de]quinolinium trifluoroacetate (makaluvamine C) in 5 ml of methyl alcohol is combined with 20 ul of benzyl bromide and 100 mg of sodium bicarbonate and stirred overnight. Chromatography on LH-20 lipophilic sephadex in methyl alcohol/0.1% TFA gives 23.7 mg of the desired product.

$^1$H NMR: 9.336(s, 1H, NH-9).

EXAMPLE 25

1,3,4,8-tetrahydro-7-[(3-methoxy-3-oxopropyl)amino]-5-methyl-8-oxo-1-(phenylmethyl)pyrrolo[4,3,2-de]quinolinium trifluoroacetate A solution of 10 mg 7-amino-1,3,4,8-tetrahydro-5-methyl-8-oxo-pyrrolo[4,3,2-de]quinolinium (makaluvamine C) in 5 ml of methyl alcohol is combined with 50 ul of methyl acrylate and 100 ul of diisopropylethylamine and stirred overnight. Chromatography on LH-20 lipophilic sephadex with methyl alcohol/0.1% TFA gives 8.6 mg of the desired product.

$^1$H NMR: 9.21(br t, j=6, 1H, NH-9), 7.53(s, 1H, CH-2), 7.25–7.39(m, 5H, N(CH$_2$C$_6$H$_5$)-1), 5.78(s, 1H, CH-6), 5.41(s, 2H, N(CH$_2$C$_6$H$_5$)-1), 3.90(t, j=7.5, 2H, CH$_2$-4), 3.61(s, 3H, N(CH$_2$CH$_2$CO$_2$CH$_3$)-9), 3.61(t, 2H, N(CH$_2$CH$_2$CO$_2$CH$_3$)-9), 3.40(d, 3H, N(Me)-5), 2.96(t, j=7.5, 2H, CH$_2$-3), 2.72(t, j=7.0, 2H, N(CH$_2$CH$_2$CO$_2$CH$_3$)-9); $^{13}$C NMR: 171.230, 167.211, 155.059, 152.971, 136.764, 130.572, 128.679, 127.987, 127.343, 123.665, 121.868, 177.862, 83.882, 52.560, 51.565, 31.594, 18.714. HR FAB MS m/z=378.1813 (M+H)$^+$, C$_{22}$H$_{24}$N$_3$O$_3$ requires 378.1818.

EXAMPLE 26

1,3,4,8-Tetrahydro-5-methyl-7-(methylamino)-8-oxo-1-(phenylmethyl)-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 5 ml of methyl alcohol is combined with 50 ul of methyl iodide and 100 ul of diisopropylethylamine and stirred overnight. Chromatography on LH-20 lipophilic sephadex with methyl alcohol/0.1% TFA gives 5.7 mg of the desired product.

$^1$H NMR: 9.21(br q, 1H,k NH-9), 7.56(s, 1H, C)(-2), 7.24–7.39(m, 5H, N(CH$_2$C$_6$H$_5$)-1), 5.61(s, 1H, CH-6), 5.42(s, 2H, N(CH$_2$C$_6$H$_5$)-1), 3.89(t, j=7.5, 2H, CH$_2$-4), 3.39(s, 3H, N(Me)-5), 2.99(d, 3H, N(Me)-9), 2.94(t, j=7.5, 2H, CH$_2$-3); $^{13}$C NMR: 167.238, 154.734, 154.054, 136.791, 130.502, 128.669 (2C), 127.977, 127.358 (2C), 123.861, 121.903, 117.864, 83.496, 52.405, 51.519, 38.820, 30.601, 18.740. HR FAB MS m/z=306.1600 (M+H)$^+$, C$_{19}$H$_{20}$N$_3$O requires 306.1606.

EXAMPLE 27 and EXAMPLE 28

1,3,4,8-Tetrahydro-1-(3-methoxy-3-oxopropyl)-7-[7-[(3-methoxy-3-oxopropyl)amino]-5-methyl-8-oxo-pyrrolo[4,3,2-de]quinolinium trifluoroacetate and 7-Amino-1,3,4,8-tetrahydro-1-(3-methoxy-3-oxopropyl)-5-methyl-8-oxo-pyrrolo[4,3,2-de]quinolinium trifluoroacetate A solution of 25 mg of 7-amino-1,3,4,8-tetrahydro-5-methyl-8-oxo-pyrrolo[4,3,2-de]quinolinium trifluoroacetate (makaluvamine C) in 5 ml of methyl alcohol is combined with 250 ul of diisopropylethylamine and 250 ul of methyl acrylate and stirred overnight. Chromatography on LH-20 lipophilic sephadex in methyl alcohol/0.1% TFA followed by silica gel flash (15% MeOH/85% CHCl$_3$/0.1% TFA) gives 30.5 mg of the first product.

$^1$H NMR: 9.007(br t, 6 Hz, 1H, NH-9), 7.379 (s, 1H, CH-2), 5.756(s , 1H, CH-6), 4.449(t, j=7.0, 2H, N(CH$_2$CH$_2$CO$_2$CH$_3$)-1), 3.894(t, j=8.0, 2H, CH$_2$-4), 3.638(dt, j=7. 0, 7.0, 2H, N(CH$_2$CH$_2$CO$_2$CH$_3$)-9), 3.605(s, 3H), 3.569 (s, 3H), 3.411(s, 3H, N(Me)-5), 2.898(t, j=8 Hz, 2H, CH$_2$-3), 2.864(t, j=7.0, 2H, N(CH$_2$CH$_2$CO$_2$CH$_3$)-1), 2.732(t, j=7.0, 2H, N(CH$_2$CH$_2$CO$_2$CH$_3$)-9); $^{13}$C NMR: 171.208, 170.649, 167.044, 155.049, 153.022, 130.490, 123.412, 122.004, 117.233, 83.763, 52.538, 51.543, 44.295, 34.098, 31.645, 18.643. HR FAB MS m/z=374.1709 (M+H)$^+$, C$_{19}$H$_{24}$N$_3$O$_5$ requires 374.1716. and $^1$H NMR: 9.402(s, 1H, NH-9), 8.636(s, 1H, NH-9), 7.351(s, 1H, CH-2), 5.679(s, 1H, CH-6), 4.446(t, j=7.0, 2H, N (CH$_2$CH$_2$CO$_2$CH$_3$)-1), 3.866(t, j=7.5, 2H, CH$_2$-4), 3.573 (s, 3H, N(CH$_2$CH$_2$CO$_2$CH$_3$)-1), 3.290(s, 3H, N(Me)-5), 2.882 (t, j-7.5, 2H, CH$_2$-3), 2.868(t, j=7.0, 2H, N(CH$_2$CH$_2$CO$_2$CH$_3$)-1); $^{13}$C NMR: 170.744, 167.539, 156.358, 155.144, 130.378, 123.568, 122.062, 117.194, 85.497, 52.391, 51.614, 44.305, 34.120, 18.750. HR FAB MS m/z =288.1345 (M+H)$^+$, C$_{15}$H$_{18}$N$_3$O$_3$ requires 288.1348.

EXAMPLE 29 AND EXAMPLE 30

7-Amino-1,3,4,8-tetrahydro-1,5-dimethyl-8-oxo-pyrrolo[4,3,2-de]quinolinium trifluoroacetate and 1,3,4,8-Tetrahydro-1,5-dimethyl-7-(methylamino)-8-oxo-pyrrolo[4,3,2-de]quinolinium trifluoroacetate A solution of 76.4 mg of 7-amino-1,3,4,8-tetrahydro-5-methyl-8-oxo-pyrrolo[4,3,2-de]quinolinium trifluoroacetate (makaluvamine C) in 5 ml of methyl alcohol is combined with 100 ul of methyl iodide and 25 mg of sodium bicarbonate and stirred overnight. Chromatography on LH-20 lipophilic sephadex in methyl alcohol/0.1% TFA followed by silica gel flash (15% MeOH/85% CHCl$_3$/0.1% TFA) gives 48 mg of the first product.

$^1$H NMR: 9.239 (s, 1H, NH-9), 8.585 (s, 1H, NH-9), 7.295(s, 1H, CH-2), 5.627(s, 1H, CH-6), 3.871(t, j=7.5, 2H, CH$_2$-4), 3.862(s, 3H, N(Me)-1), 3.292(s, 3H, N(Me)-5), 2.887(t, j=2.872, 2H, CH$_2$-3); $^{13}$C NMR: 167.685, 156.297, 155.120, 130.997, 123.094, 122.463, 117.255, 85.508, 52.336, 38.830, 35.868, 18.750; HR FAB MS m/z=216.1135 (M+H)$^+$, C$_{12}$H$_{14}$N$_3$O requires 216.1137. and 7.1 mg of the second product.

$^1$H NMR: 9.186(br q, j=5.5, 1H, NH-9), 7.319(s, 1H, CH-2), 5.583(s, 1H, CH-6), 3.890(t, j=7.5, 2H, CH$_2$-4), 3.888(s, 3H, N(Me)-1), 3.400(s, 3H, N(Me)-5), 3.004(d, j=5.5 Hz, 3H, N(Me)-9), 2.910(t, j=7.5, 2H, CH$_2$-3); HR FAB MS m/z=230.1302 (M+H)$^+$, C$_{13}$H$_{16}$N$_3$O requires 230.1293.

EXAMPLE 31

7-Amino-1,3,4,8-tetrahydro-1-methyl-8-oxo-5-(2-propenyl)[4,3,2-de]quinolinium trifluoroacetate A solution of 10 mg of 7-amino-3,4-dihydro-1-methyl-pyrrolo[4,3,2-de]quinolin-8 (1H)-one trifluoroacetate (makaluvamine A) in 5 ml of methyl alcohol is combined with 15 ul of allyl iodide and 25 mg of sodium bicarbonate and stirred overnight. Chromatography on LH-20 lipophilic sephadex in methyl alcohol/0.1% TFA followed by silica gel flash (15% MeOH/85% CHCl$_3$/0.1% TFA) gives 8.9 mg of the desired product.

$^1$H NMR: 9.396(s, 1H, NH-9), 8.723(s, 1H, NH-9), 7.325(s, 1H, CH-2), 6.00(br m, 1H, N(CH$_2$CHCH$_2$)-5), 5.688(s, 1H, CH-6), 5.326(d, j=9 Hz, 1H, N(CH$_2$CHC(H$_{cis}$)H$_{trans}$))-5), 5.302(d, j=15.5 Hz, 1H, N(CH$_2$CHC(H$_{cis}$)H$_{trans}$))-5), 4.286(d, j=5 Hz, 2H, N(CH$_2$CHCH$_2$)-5), 3.890(s, 3H, N(Me)-1), 3.873(t, j=7.5, 2H, CH$_2$-4), 2.909(t, j=7.5, 2H, CH$_2$-3).

EXAMPLE 32

7-Amino-1,3,4,8-tetrahydro-1-methyl-8-oxo-5-(phenylmethyl)-pyrrolo[4,3,2-de]quinolinium trifluoroacetate A solution of 10 mg of 7-amino-3,4-dihydro-1-methyl-pyrrolo[4,3,2-de]quinolin-8(1H)-one trifluoroacetate (makaluvamine A) in 5 ml of methyl alcohol is combined with 20 ul of benzyl bromide and 25 mg of sodium bicarbonate and stirred overnight. Chromatography on LH-20 lipophilic sephadex in methyl alcohol/0.1% TFA followed by silica gel flash (15% MeOH/85% CHCl$_3$/0.1% TFA) gives 8.9 mg of the desired product.

$^1$H NMR: 9. 438 (s, 1H, NH-9), 8.763 (s, 1H, NH-9), 7.32–7.42(m, 6H, CH-2 and N(CH$_2$C$_6$H$_5$)-5), 5.819(s, 1H, CH-6), 4.883(s, 2H, N(CH$_2$C$_6$H$_5$)-5), 3.891(t, j=7.5, 2H, CH$_2$-4), 3.880(s, 3H, N(Me)-1), 2.892(t, j=7.5, 2H, CH$_2$-3); HR FAB MS m/z=292.1450 (M+H)$^+$, C$_{18}$H$_{18}$N$_3$O requires 292.1450.

EXAMPLE 33 AND EXAMPLE 34

7-Amino-1,3,4,8-tetrahydro-1-methyl-8-oxo-5,6-bis(-phenylmethyl-pyrrolo-[4,3,2-de]quinolinium trifluoroacetate and 1,3,4,8-Tetrahydro-1-methyl-8-oxo-5-(phenylmethyl)-7-[(phenylmethyl) amino]pyrrolo[4,3,2-de]quinolinium trifluoroacetate A solution of 25 mg of 7-amino-3,4-dihydro-1-methyl-pyrrolo[4,3,2-de]quinolin-8(1H)-one trifluoroacetate (makaluvamine A) in 10 ml of methyl alcohol is combined with 100 ul of benzyl bromide and 50 mg of sodium bicarbonate and stirred overnight. Chromatography on LH-20 lipophilic sephadex in methyl alcohol/0.1% TFA followed by silica gel flash (15% MeOH/85% CHCl$_3$/0.1% TFA) gives 21.2 mg of the first desired product.

$^1$H NMR: 8.8–9.2(br s, 2H, NH$_2$-9), 7.0–7.4(m, 11H, CH-2 and N(CH$_2$C$_6$H$_5$)-5) and C(CH$_2$C$_6$H$_5$)-6, 5.819(s, 1H, CH-6), 4.734(s, 2H, N(CH$_2$C$_6$H$_5$)-5), 3.933(s, 3H, N(Me)-1), 3.770(t, j=7.0, 2H, CH$_2$-4), 3.318(s, 2H, C(CH$_2$C$_6$H$_5$)-6), 2.755(t, j=7.0, 2H, CH$_2$-3); HR FAB MS m/z=382.1905 (M+H)$^+$, C$_{25}$H$_{24}$N$_3$O requires 382.1919 and 3.8 mg of the second desired product.

$^1$H NMR: 9.791(s, j=6.0 Hz, 1H, NH-9), 7.2–7.3(m, 11H, CH-2 and N(CH$_2$C$_6$H$_5$)-5 and N(CH$_2$C$_6$H$_5$)-9), 5.974(s, 1H, CH-6), 4,966(s, 2H, N(CH$_2$C$_6$H$_5$)-5), 4.686(d, j=6.0 Hz, 2H, N(CH$_2$C$_6$H$_5$)-9), 3.900(s, 3H, N(Me)-1), 3.846(t, j=8.0, 2H, CH$_2$-4), 2.864(t, j=8.0, 2H, CH$_2$-3); HR FAB MS m/z=382 1904 (M+H)$^+$, C$_{25}$H$_{24}$N$_3$O requires 382.1919.

EXAMPLE 35

1,3,4,8-Tetrahydro-5-methyl-7-(methylamino)-8-oxopyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 1 ml of degassed methyl alcohol is stirred for two hours under nitrogen with rigorous exclusion of oxygen. This mixture is then treated with 5 mg of NaBH$_4$ followed by treatment with 50 ul of methyl iodide. Chromatography on LH-20 lipophilic sephadex in methyl alcohol/0.1% TFA followed by silica gel flash (15% MeOH/85% CHCl$_3$/0.1% TFA) gives 8.9 mg of the desired product.

$^1$H NMR: 13,066(s, 1H, NH-1), 9.250(br q, 4 Hz, 1H, NH-9), 7.312(br d, 1H, CH-2), 5.582(s, 1H, CH-6), 3.912 (t. j=7.5 Hz, 2H, CH$_2$-4), 3.412 (s, 3H, N (Me)-5), 3.002(br d, j=6 Hz, 3H, N(CH₃)-9), 2.931(t, j=7.5, 2H, CH₂-3).

EXAMPLE 36

1,3,4,8-Tetrahydro-5-methyl-7-(methyl-d-amino)-8-oxo-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 1 ml of degassed methyl alcohol is stirred for two hours under nitrogen with rigorous exclusion of oxygen. This mixture is then treated with 20 mg of NaBD₄ followed by treatment with 13 ul of formaldehyde. Chromatography on LH-20 lipophilic sephadex in methyl alcohol/0.1% TFA followed by silica gel flash (15% MeOH/85% CHCl₃/0.1% TFA) gives 3.2 mg of the desired product.

$^1$H NMR: 13,061(s, 1H, NH-1), 9.235(br t, 5 Hz, 1H, NH-9), 7.314(d, j=3.5 Hz, 1H, CH-2), 5.585(s, 1H, CH-6), 3.916(t, j=8.0 Hz, 2H, CH₂-4), 3.414(s, 3H, N(Me)-5), 2.994(m, 2H, N(CH₂D)-9), 2.935(t, j=8.0, 2H, CH₂-3); HR FAB MS m/z=217.1089 (M+H)+, C₁₂H₁₃DN₃O requires 217. 1199.

EXAMPLE 37

1,3,4,8-tetrahydro-7-[(3-methoxy-3-oxopropyl)amino]-5-methyl-8-oxo-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 1 ml of degassed methyl alcohol is stirred for two hours under nitrogen with rigorous exclusion of oxygen. This mixture is then treated with 5 mg of NaBH₄ followed by treatment with 100 ul of methyl acrylate. Chromatography on LH-20 lipophilic sephadex in methyl alcohol/0.1% TFA followed by silica gel flash (15% MeOH/85% CHCl₃/0.1% TFA) gives 0.9 mg of the desired product.

$^1$H NMR: 13,067(s, 1H, NH-1), 9.029(br t, 1H, NH-9), 7.319(d, j=3.0 Hz, 1H, CH-2), 5.755(s, 1H, CH-6), 3.926(t, j=7.5 Hz, 2H, CH₂-4), 3.642(dt, j=6.0, 7.0, 2H, N(CH₂CH₂CO₂CH₃)-9), 3.621(s, 3H, N(CH₂CH₂CO₂CH₃)-9), 3.431(s, 3H, N(Me)-5), 2.936(t, j=7.5, 2H, CH₂-3), 2.751(t, j=6.0 Hz, 2H, N(CH₂CH₂CO₂CH₃)-9); HR FAB MS m/z=288.1343 (M+H)+, C₁₅H₁₈N₃O₃ requires 288.1348.

EXAMPLE 38 AND EXAMPLE 39

1,3,4,8-Tetrahydro-5-methyl-7-(octylamino)-8-oxo-pyrrolo[4,3,2-de]quinolinium trifluoroacetate and 1,3,4,8-Tetrahydro-5-methyl-7-(dioctylamino)-8-oxo-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 1 ml of degassed methyl alcohol is stirred for two hours under nitrogen with rigorous exclusion of oxygen. This mixture is then treated with 5 mg of NaBH₄ followed by treatment with 50 ul of octyl aldehyde. Chromatography on LH-20 lipophilic sephadex in methyl alcohol/0.1% TFA followed by silica gel flash (15% MeOH/85% CHCl₃/0.1% TFA) gives 2.3 mg of the first desired product.

$^1$H NMR: 13,043(s, 1H, NH-1), 9.190(br t, j=5.5 Hz, 1H, NH-9), 7.312(d, j=2.5 Hz, 1H, CH-2), 5.664(s, 1H, CH-6), 3.902(t, j=7.0 Hz, 2H, CH₂-4), 3.414(m, 2H, N(CH₂(C₇H₁₅))-9), 3.404(s, 3H, N(Me)-5), 2.926(t, j=7.0 Hz, 2H, CH₂-3), 0.8–1.6(m, 15H, NCH₂(C₇H₁₅)-9); HR FAB MS m/z=314 2225 (M+H)+, C₁₉H₂₈N₃O requires 314.2232. and 11.1 mg of the second desired product.

$^1$H NMR: 12,850(s, 1H, NH-1), 7.221(d, j=2.5 Hz, 1H, CH-2), 5.565(s, 1H, CH-6), 3.888(t, j=S.0 Hz, 2H, CH₂-4), 3.5–4.0(m, 4H, N(CH₂(C₇H₁₅))2-9), 3.380(s, 3H, N(Me)-5), 2.924(t, j=8.0 Hz, 2H, CH₂-3), 0.8–1.6(m, 30H, N(CH₂(C₇H₁₅) )2-9); HR FAB MS m/z=426.3477 (M)+, C₂₇H₄₄N₃O requires 426.3484.

EXAMPLE 40

1,3,4,8-Tetrahydro-5-methyl-7-[(2-methylethyl)amino]-8-oxo-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 1 ml of degassed methyl alcohol is stirred for two hours under nitrogen with rigorous exclusion of oxygen. This mixture is then treated with 5 mg of NaBH₄ followed by treatment with 25 ul of acetone. Chromatography on LH-20 lipophilic sephadex in methyl alcohol/0.1% TFA followed by silica gel flash (15% MeOH/85% CHCl₃/0.1% TFA) gives 10.7 mg of the first desired product.

$^1$H NMR: 13,074(s, 1H, NH-1), 8.882(br d, 2.5 Hz, 1H, NH-9), 7.300(d, j=2.5 Hz, 1H, CH-2), 5.709(s, 1H, CH-6), 4.142(m, 1H, N(CH(CH₂)5)-9), 3.907(t, j=8.0 Hz, n2H, CH₂-4), 3.416(s, 3H, N(Me)-5), 2.928(t, j=8.0 Hz, 2H, CH₂-3), 1.5–2.0(m, 10H, N(CH(CH₂)5)-9).

EXAMPLE 41

7-(Cyclohexylamino)-1,3,4,8-tetrahydro-5-methyl-8-oxo-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 1 ml of degassed methyl alcohol is stirred for two hours under nitrogen with rigorous exclusion of oxygen. This mixture is then treated with 5 mg of NaBH₄ followed by treatment with 30 ul of cyclohexanone. Chromatography on LH-20 lipophilic sephadex in methyl alcohol/0.1% TFA followed by silica gel flash (15% MeOH/85% CHCl₃/0.1% TFA) gives 12.4 mg of the first desired product.

$^1$H NMR: 13,078(s, 1H, NH-1), 8.824(br d, 4.0 Hz, 1H, NH-9), 7.307(d, j=3.0 Hz, 1H, CH-2), 5.717(s, 1H, CH-6), 4.073(m, 1H, N(CH(CH₃)2)-9), 3.900(t, j=7.5 Hz, 2H, CH₂-4), 3.407(s, 3H, N(Me)-5), 2.924(t, j=7.5 Hz, 2H, CH₂-3), 1.252(d, j=7.0 Hz, 6H, N(CH(CH₃)2)-9); HR FAB MS m/z=244.1443 (M+H)+, C₁₄H₁₈N₃O requires 244.1450.

EXAMPLE 42

7-(Dimethylamino )-1,3,4,8-tetrahydro-5-methyl-8-oxo-pyrrolo[4,3,2-de]-quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 1 ml of degassed methyl alcohol is stirred for two hours under nitrogen with rigorous exclusion of oxygen. This mixture is then treated with 5 mg of NaBH₄ followed by treatment with 25 ul of 40% w/v formaldehyde. Chromatography on LH-20 lipophilic sephadex in methyl alcohol/0.1% TFA followed by silica gel flash (15% MeOH/85% CHCl₃/0.1% TFA) gives 2.3 mg of the first desired product.

$^1$H NMR: 12.874(s, 1H, NH-1), 7.226(d, j=3.5 Hz, 1H, CH-2), 5.615(s, 1H, CH-6), 3.897(t, j=7.0 Hz, 2H, CH$_2$-4), 3.397(s, 3H, N(Me)-5), 2.933(t, j=7.0 Hz, 2H, CH$_2$-3), 2.491(m, 6H, N(CH$_3$)$_2$-9); HR FAB MS m/z=230.1289 (M)$^+$, C$_{13}$H$_{16}$N$_3$O requires 230.1293.

EXAMPLE 43

7-[(3-Furanylmethyl)amino]-1,3,4,8-tetrahydro-5-methyl-8-oxo-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 1 ml of degassed methyl alcohol is stirred for two hours under nitrogen with rogorous exclusion of oxygen. This mixture is then treated with 5 mg of NaBH$_4$ followed by treatment with 25 ul of 2-furaldehyde. Chromatography on LH-20 lipophilic sephadex in methyl alcohol/0.1% TFA followed by silica gel flash (15% MeOH/85% CHCl$_3$/0.1% TFA) gives 8.7 mg of the first desired product.

$^1$H NMR: 13.085(s, 1H, NH-1), 9.418(br t, j=6.0 Hz, 1H, NH-9), 7.631(br d, j=3.0 Hz, 1H, CH-2), 7.305(br d, j=3.5 Hz, 1H, N(CH$_2$C$_3$H$_3$O)-9), 6.487(br d, j=3.5 Hz, 1H, N(CH$_2$C$_3$H$_3$O)-9), 6.426(dd, j=3.5, 3.5 Hz, 1H, N(CH$_2$C$_3$H$_3$O)-9), 5.854(s, 1H, CH-6), 4.668(br d, j=7.0 Hz, 2H, N(CH$_2$C$_3$H$_3$O)-9), 3.931(t, j=8.0 Hz, 2H, CH$_2$-4), 3.412(s, 3H, N(Me)-5), 2.931(t, j=8.0 Hz, 2H, CH$_2$-3); HR FAB MS m/z=282 1244 (M+H)$^+$, C$_{16}$H$_{16}$N$_3$O$_2$ requires 282.1243.

EXAMPLE 44

1,3,4,8-Tetrahydro-5-methyl-7-[(1-naphthalenylmethyl)amino]-8-oxo-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 1 ml of degassed methyl alcohol is stirred for two hours under nitrogen with rigorous exclusion of oxygen. This mixture is then treated with 5 mg of NaBH$_4$ followed by treatment with 34 ul of 1-naphthaldehyde. Chromatography on LH-20 lipophilic sephadex in methyl alcohol/0.1% TFA followed by silica gel flash (15% MeOH/85% CHCl$_3$/0.1% TFA) gives 14.0 mg of the first desired product.

$^1$H NMR: 13,127(s, 1H, NH-1), 9.606(br t, j=6.0 Hz, 1H, NH-9), 7.4–8.2(m, 7H, N(CH$_2$(C$_{10}$H$_7$)-9), 7.310(br d, j=2.5 Hz, 1H, CH-2), 5.774(s, 1H, CH-6), 5.152(br d, j=5 Hz, 2H, N(CH$_2$(C$_{10}$H$_7$)-9), 3.890(t, j=7.5 Hz, 2H, CH$_2$-4), 3.296(s, 3H, N(Me)-5), 2.914(t, j=7.5, 2H, CH$_2$-3); HR FAB MS m/z=342.1599 (M+H)$^+$, C$_{22}$H$_{20}$N$_3$O requires 342.1606.

EXAMPLE 45

7-[[(4-Carboxylphenyl)methyl]amino]-1,3,4,8-tetrahydro-5-methyl-8-oxo-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 1 ml of degassed methyl alcohol is stirred for two hours under nitrogen with rigorous exclusion of oxygen. This mixture is then treated with 5 mg of NaBH$_4$ followed by treatment with 50 mg of carboxybenzaldehyde. Chromatography on LH-20 lipophilic sephadex in methyl alcohol/0.1% TFA followed by silica gel flash (15% MeOH/85% CHCl$_3$/0.1% TFA) gives 9.7 mg of the first desired product.

$^1$H NMR: 13.098(s, 1H, NH-1), 9.663(br t, j=7.0 Hz, 1H, NH-9), 7.923(br d, j=7.0 Hz, 2H, N(CH$_2$C$_6$H$_4$CO$_2$H)-9), 7.493(br d, j=7.0 Hz, 2H, N(CH$_2$C$_6$H$_4$CO$_2$H)-9), 7.308(br d, j=2.5 Hz, 1H, CH-2), 5.705(s, 1H, CH-6), 4.745(br d, j=7.0 Hz, 2H, N(CH$_2$C$_6$H$_4$CO$_2$H)-9), 3.902(t, j=8.0 Hz, 2H, CH$_2$-4), 3.332(s, 3H, N(Me)-5), 2.916(t, j=8.0, 2H, CH$_2$-3); HR FAB MS m/z=336.1343 (M+H)$^+$, C$_{19}$H$_{18}$N$_3$O$_3$ requires 336.1348.

EXAMPLE 46

1,3,4,8-Tetrahydro-5-methyl-8-oxo-7-[(phenylmethyl)amino]-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 1 ml of degassed methyl alcohol is stirred for two hours under nitrogen with rigorous exclusion of oxygen. This mixture is then treated with 5 mg of NaBH$_4$ followed by treatment with 50 ul of benzyl bromide. Chromatography on LH-20 lipophilic sephadex in methyl alcohol/0.1% TFA followed by silica gel flash (15% MeOH/85% CHCl$_3$/0.1% TFA) gives 3.3 mg of the first desired product.

$^1$H NMR: 13.062(s, 1H, NH-1), 9.651(br t, 6 Hz, 1H, NH-9), 7.26–7.40(m, 6H, N(CH$_2$C$_6$H$_5$)-9 and CH-2), 5.726(s, 1H, CH-6), 4.673(d, j=7.0 Hz, 2H, N(CH$_2$C$_6$H$_5$)-9), 3.894(t, j=7.5 Hz, 2H, CH$_2$-4), 3.340(s, 3H, N(Me)-5), 2.912(t, j=7.5, 2H, CH$_2$-3); HR FAB MS m/z =292.1447 (M+H)$^+$, C$_{18}$H$_{18}$N$_3$O requires 292.1450.

EXAMPLE 47

1,3,4,8-Tetrahydro-7-[[(4-hydroxy-3-methoxyphenyl)methyl]amino]-5-methyl-8-oxo-pyrrolo[4,3,2-de]quinolin-8 (1H)-one trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 1 ml of degassed methyl alcohol is stirred for two hours under nitrogen with rigorous exclusion of oxygen. This mixture is then treated with 5 mg of NaBH$_4$ followed by treatment with 50 mg of 4-methoxy-3-hydroxybenzaldehyde. Chromatography on LH-20 lipophilic sephadex in methyl alcohol/0.1% TFA followed by silica gel flash (15% MeOH/85% CHCl$_3$/0.1% TFA) gives 2.8 mg of the desired product.

$^1$H NMR: 13.045(s, 1H, NH-1), 9.572(br t, j=6.0 Hz, 1H, NH-9), 8.983(br s, 1H, N(CH$_2$C$_6$H$_3$ (OCH$_3$)OH)-9), 7.300(s, 1H, CH-2), 7.043(s, 1H, N(CH$_2$C$_6$H$_3$(OCH$_3$)OH)-9), 6.812(d, ju=7.5 Hz, 1H, N(CH$_2$C$_6$H$_3$(OCH$_3$)OH)-9), 6.725(dd, j=7.5, 2.0 Hz, 1H, N(CH$_2$C$_6$H$_3$(OCH$_3$)OH)-9), 5.738(s, 1H, CH-6), 4.520(br d, 2H, N(CH$_2$C$_6$H$_3$(OCH$_3$)OH)-9), 3.890(t, j=8.0 Hz, 2H, CH$_2$-4), 3.741(s, 3H, N(CH$_2$C$_6$H$_3$(OCH$_3$)OH)-9), 3.364(s, 3H, N(Me)-5), 2.911(t, j=8.0, 2H, CH$_2$-3).

EXAMPLE 48

1,3,4,8-Tetrahydro-7- [[(4-methoxyphenyl)methyl]amino]-5-methyl-8-oxo-pyrrolo[4,3,2-de]-quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 1 ml of degassed methyl alcohol is stirred for two hours under nitrogen with rigorous exclusion of oxygen. This mixture is then treated with 5 mg of NaBH$_4$ followed by treatment with 40 ul of 4-methoxybenzaldehyde. Chromatography on LH-20 lipophilic sephadex in methyl alcohol/0.1% TFA followed by silica gel flash (15% MeOH/85% CHCl$_3$/0.1% TFA) gives 13.5 mg of the desired product.

$^1$H NMR: 13,085(s, 1H, NH-1), 9.620(br t, j=6.0 Hz, 1H, NH-9), 7.338(d, j=8.5 Hz, 2H, N(CH$_2$C$_6$H$_4$OCH$_3$)-9), 7.299(br d, j=3.0 Hz, 1H, CH-2), 6.908(d, j=8.5 Hz, 2H, N(CH$_2$C$_6$H$_4$OCH$_3$)-9), 5.729(s, 1H, CH-6), 4.583(br d, j=6.0 Hz, 2H, N(CH$_2$C$_6$H$_4$OCH$_3$)-9), 3.894(t, j=8.0 Hz, 2H, CH$_2$-4), 3.721(s, 3H, N(CH$_2$C$_6$H$_4$OCH$_3$)-9), 3.358(s, 3H, N(Me)-5), 2.909 (t j=8 0 2H CH$_2$-3); HR FAB MS m/z=322.1546 (M+H)$^+$, C$_{19}$H$_{20}$N$_3$O$_2$ requires 322.1556.

EXAMPLE 49

1,3,4,8-Tetrahydro-7-[[(4-hydroxyphenyl)methyl]amino]-5-methyl-8-oxo-pyrrolo[4,3,2-de]quinolin-8 (1H)-one trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 1 ml of degassed methyl alcohol is stirred for two hours under nitrogen with rigorous exclusion of oxygen. This mixture is then treated with 5 mg of NaBH$_4$ followed by treatment with 50 mg of 4-hydroxybenzaldehyde. Chromatography on LH-20 lipophilic sephadex in methyl alcohol/0.1% TFA followed by silica gel flash (15% MeOH/85% CHCl$_3$/0.1% TFA) gives 4.0 mg of the desired product.

$^1$H NMR: 13,066(s, 1H, NH-1), 9.581(br t, j=6.0 Hz, 1H, NH-9), 7.303(br d, j=2.5 Hz, 1H, CH-2), 7.209(d, j=9.0 Hz, 2H, N(CH$_2$C$_6$H$_4$OH)-9), 6.724(d, j=9.0 Hz, 2H, N(CH$_2$C$_6$H$_4$OH)-9), 5.719(s, 1H, CH-6), 4,529(br d, j=6.0 Hz, 2H, N(CH$_2$C$_6$H$_4$OH)-9), 3.982(t, j=8.0 Hz, 2H, CH$_2$-4), 3.356(s, 3H, N(Me)-5), 2.911(t, j=8.0, 2H, CH$_2$-3); HR FAB MS m/z=308.1408 (M+H)$^+$, C$_{18}$H$_{18}$N$_3$O$_2$ requires 308.1399.

EXAMPLE 50

7-[[[4-(Dimethylamino)phenyl]methyl]amino]-1,3,4,8-tetrahydro-5-methyl-8-oxo-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 1 ml of degassed methyl alcohol is stirred for two hours under nitrogen with rigorous exclusion of oxygen. This mixture is then treated with 5 mg of NaBH$_4$ followed by treatment with 50 mg of 4-(dimethylamino)benzaldehyde. Chromatography on LH-20 lipophilic sephadex in methyl alcohol/0.1% TFA followed by silica gel flash (15% MeOH/85% CHCl$_3$/0.1% TFA) gives 1.0 mg of the desired product.

$^1$H NMR: 13.070(s, 1H, NH-1), 9,592(br t, j=6.0 Hz, 1H, NH-9), 7.305(br d, j=2.5 Hz, 1H, CH-2), 7.235(d, j=9.0 Hz, 2H, N(CH$_2$C$_6$H$_4$N(CH$_3$)2)-9), 6.692(d, j=9.0 Hz, 2H, N(CH$_2$C$_6$H$_4$N(CH$_3$)2)-9), 5.740(s, 1H, CH-6), 4.524(br d, j=4.5 Hz, 2H, N(CH$_2$C$_6$H$_4$N(CH$_3$)2)-9), 3.890(t, j=7.0 Hz, 2H, CH$_2$-4), 3.363(s, 3H, N(Me)-5), 2.911(t, j=7.0, 2H, CH$_2$-3), 2.861(s, 6H, N(CH$_2$C$_6$H$_4$N(CH$_3$)2)-9); HR FAB MS m/z=308.1408 (M+H)$^+$, C$_{18}$H$_{18}$N$_3$O$_2$ requires 308.1399.

EXAMPLE 51

1,3,4,5-Tetrahydro-1-methyl-pyrrolo[4,3,2-de]quinoline-7,8-dione trifluoroacetate A solution of 10 mg of 7-amino-3,4-dihydro-1-methyl-pyrrolo[4,3,2-de]quinolin-8 (1H)-one (makaluvamine) in 5 ml of 25% aqueous sulfuric acid is stirred overnight at room temperature. Chromatography on LH-20 lipophilic sephadex in methyl alcohol/0.1% TFA followed by silica gel flash (15% MeOH/85% CHCl$_3$/0.1% TFA) gives 5.2 mg of the desired product.

$^1$H NMR: 8.232(s, 1H, NH-5), 7.067(s, 1H, CH-2), 5.006(s, 1H, CH-6), 3.809(s, 3H, N(Me)-1), 3.457(dt, j=2.5, 6.5 HZ, 2H, CH$_2$-4), 3.289(s, 3H, N(Me)-5), 2.672(t, j=6.5, 2H, CH$_2$-3).

EXAMPLE 52

1,3,4,5-Tetrahydro-1,5-dimethyl-pyrrolo[4,3,2-de]-quinoline-7,8-dione

A solution of 7-amino-1,3,4,8-tetrahydro-5-methyl-1,5-dimethyl-8-oxo-pyrrolo[4,3,2-de]quinolin-8(1H)-one trifluoroacetate in 5 ml of 25% aqueous sulfuric acid is stirred overnight at room temperature. Chromatography on LH-20 lipophilic sephadex in methyl alcohol/0.1% TFA followed by silica gel flash (15% MeOH/85% CHCl$_3$/0.1% TFA) gives 5.8 mg of the desired product.

$^1$H NMR: 7.077(s, 1H, CH-2), 5.162(s, 1H, CH-6), 3.817(s, 3H, N(Me)-1), 3.577(t, j=6.5, 2H, CH$_2$-4), 3.025(s, 3H, N(Me)-5), 2.769(t, j=6.5, 2H, CH$_2$-3); HR FAB MS m/z=217.0987 (M+H)$^+$, C$_{12}$H$_{13}$N$_2$O$_2$ requires 217.0977.

EXAMPLE 53

1,3,4,5-Tetrahydro-5-methyl-pyrrolo[4,3,2-de]quinoline-7,8-dione trifluoroacetate A solution of 20 mg of 7-amino-1,3,4,8-tetrahydro-5-methyl-8-oxo-pyrrolo[4,3,2-de]quinolinium trifluoroacetate (makaluvamine C) in 5 ml of 25% aqueous sulfuric acid is stirred overnight. Chromatography on LH-20 lipophilic sephadex in methyl alcohol/0.1% TFA followed by silica gel flash (15% MeOH/85% CHCl$_3$/0.1% TFA) gives 8.1 mg of the desired product.

EXAMPLE 54 AND EXAMPLE 55

3,5,6,7-Tetrahydro-1,8,9-trimethyl-6-oxo-2M-dipyrrolo[4,3,2-de:2',3'-h]quinolinium trifluoroacetate and 7,7'-[(1,2-dimethyl-1,2-ethanediyl)diimino]bis[1,3,4,8-tetrahydro-5-methyl-8-oxo-pyrrolo[4,3,2-de]-quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 15 ml of degassed methyl alcohol is stirred for two hours under nitrogen with rigorous exclusion of oxygen. This mixture is treated with 25 mg of NaBH$_4$ followed by treatment with 100 ul of 2,3-butanedione. Chromatography on LH-20 lipophilic sephadex in methyl alcohol/0.1% TFA followed by silica gel flash (15% MeOH/85% CHCl₃/0.1% TFA) gives 10.7 mg of the first desired product.

¹H NMR: 12.986(s, 1H, NH-8), 12.895(s, 1H, NH-1), 7.048(s, 1H, CH-2), 4.091(t, j=7.5 Hz, 2H, CH₂-4), 3.697(s, 3H, N(CH₃)-5), 2.958(t, j=7.5, 2H, CH₂-3), 2.195(s, 3H, C(CH₃)-6), 2.177(s, 3H, C(CH₃)-7). and 17.1 mg of the second desired product as a mixture of a pair of enantiomeric compounds and a meso compound.

¹H NMR: 12.319 (br s, 2H, NH-1), 10. 029 (br m, 2H, NH-9), 6.856(br s, 2H, CH-2), 5.430(br s, 2H, CH-6), 3.98(br m, 2H, N(CH(CH₃))-9), 3.767(br m, 4H, CH₂-4), 3.226(br s, 6H, N(CH₃)-5), 2.907(br m, 4H, CH₂-3), 1.494(br s, 3H, N(CH(CH₃))-9), 1.167 (br s, 3H, N(CH(CH₃) )-9).

EXAMPLE 56

7-Amino-1-(2-cyanoethyl)-1,3,4,8-tetrahydro-5-methyl-8-oxo-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) is dissolved in 1 ml of methyl alcohol and combined with 25 mg of potassium carbonate with 25 mg of potassium carbonate and 50 ul of acrylonitrile and stirred overnight. Chromatography on LH-20 lipophilic sephadex in methyl alcohol/0.1% TFA followed by silica gel flash (15% MeOH/85% CHCl₃/0.1% TFA) gives 4.7 mg of the desired product.

¹H NMR: 9. 358 (s, 1H, NH-9), 8. 694 (s, 1H, NH-9), 7.440(s, 1H, CH-2), 5.685(s, 1H, CH-6), 4.515(t, j=6.0, 2H, N(CH₂CH₂CN)-1), 3.907(t, j=7.5, 2H, CH₂-4), 3.323(s, 3H, N(CH₃)-5), 3.094(t, j=6.0, 2H, N(CH₂CH₂CN-1), 2.936(t, j=7.5 Hz, 2H, CH₂-3), HR FAB MS m/z=255 1245 (M+H)+, C₁₄H₁₅N₄O requires 255. 1246.

EXAMPLE 57

7,7'-(1,4-Dimethyl-1,4-butanediyldiimino)-bis[1,3,4,8-tetrahydro-5-methyl-8-oxo-pyrrolo[4,3,2-de]-quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 1 ml of degassed methyl alcohol is stirred for two hours under nitrogen with rigorous exclusion of oxygen. This mixture is treated with 5 mg of NaBH₄ followed by treatment with 37 ul of acetonylacetone. Chromatography on LH-20 lipophilic sephadex in methyl alcohol/0.1% TFA followed by silica gel flash (15% MeOH/85% CHCl₃/0.1% TFA) gives 7.5 mg of the desired product as a mixture of a pair of enantiomeric compounds and a meso compound.

¹H NMR:13.074(br s, 2H, NH-1), 8.555(br m, 2H, NH-9), 7.313(br s, 2H, CH-2), 5.753(s, 1H, CH-6), 5.733(s, 1H, CH-6), 3.94(br m, 1H, N(CH(CH₃)CH₂)-9), 3.899(t, j-7.5 Hz, 4H, CH₂-4), 3.57(m, 1H, N(CH(CH₃)CH₂)-9), 3.397(br s, 6H, N(CH₃)-5), 2.924(t, J=7.5 Hz, 4H, CH₂-3), 1.5–1.9(m, 2H, N(CH(CH₃)CH₂)-9), 1.305(d, 7.0 Hz, 6H, N(CH(CH₃)CH₂)-9), 1.033 and 1.026(d, j=7.0 Hz, 3H, N(CH(CH₃)CH₂)-9).

EXAMPLE 58

1,3,4,8-Tetrahydro-7-[2-hydroxy-2-phenylethyl)amino]-5-methyl-8-oxo-pyrrolo[4,3,2-de]quinolinium trifluoroacetate A solution of 10 mg of 7-amino-1,3,4,8-tetrahydro-5-methyl-8-oxo-pyrrolo[4,3,2-de]quinolinium trifluoroacetate (makaluvamine C) in 1 ml of degassed methyl alcohol is stirred for two hours under nitrogen with rigorous exclusion of oxygen. This mixture is then treated with 4 mg of NaBH₄ followed by treatment with 48 mg of phenylglyoxal monohydrate. Chromatography on LH-20 lipophilic sephadex in methyl alcohol/0.1% TFA followed by silica gel flash (15% MeOH/85% CHCl₂/0.1% TFA) gives 13.0 mg of the desired product. ¹H NMR: 13.133(s, 1H, NH-1), 8.763(t, j=6.0 Hz, 1H, NH-9), 7.26–7.46(m, 6H, N(CH₂CH(OH)C₆H₅)-9 and CH-2), 5.710(s, 1H, CH-6), 4.935(dd, j=8.5, 5.0 Hz, 2H, N(CH₂CH(OH)C₆H₅)-9), 3.903(t, j=7.5 Hz, 2H, CH₂-4), 3.593(m, 1H, N(CH₂CH(OH)C₆H₅)-9), 3.279(s, 3H, N(CH₃)-5), 2.922(t, j=7.5 Hz, 2H, CH₂-3).

EXAMPLE 59

1,3,4,8-Tetrahydro-5-methyl-7-[(2-phenylethenyl)amino]-8-oxo-pyrrolo[4,3,2-de]quinolinium trifluoroacetate A solution of 5 mg 1,3,4,8-Tetrahydro-7- [(2-hydroxy-2-phenylethyl)-amino]-5-methyl-8-oxo-pyrrolo[4,3,2-de]quinolinium (Example 58) in 1 ml of pyridine is treated with 100 ul of trifluoroacetic anhydride. Chromatography on LH-20 lipophilic sephadex in methyl alcohol/0.1% TFA gives 4.0 mg of the desired product.

¹H NMR: 13.156(s, 1H, NH-1), 9.099(d, j=9.0 Hz, 1H, NH-9), 7.2–7.5(m, 8H, N(CHCHC₆H₅)-9 and CH-2), 5.615(s, 1H, CH-6), 3.900(t, j=7.5 Hz, 2H, CH₂-4), 3.309(s, 3H, N(CH₃)-5), 2.905(t, j=7.5 Hz, 2H, CH₂-3).

EXAMPLE 60

1,3,4,8-Tetrahydro-5-methyl-8-oxo-7-[(phenylmethyl)amino]pyrrolo[4,3,2-de]quinolinium trifluoroacetate A solution of 10 mg of damirone B is dissolved in 1 ml of degassed methyl alcohol and stirred for two hours under argon with rigorous exclusion of oxygen. The mixture is treated with 50 ul of benzylamine under argon for 18 hours. Chromatography on LH-20 lipophilic sephadex in methyl alcohol/0.1% TFA followed by silica gel flash (15% MeOH/85% CHCl₃/0.1% TFA) gives 13.9 mg of the desired product.

EXAMPLE 61

1,3,4,8-Tetrahydro-5-methyl-7-(methylamino)-8-oxo-pyrrolo[4,3,2-de]quinolinium trifluoroacetate A solution of 10 mg of damirone B is dissolved in 1 ml of degassed methyl alcohol and stirred for two hours under argon with rigorous exclusion of oxygen. The mixture is treated with 50 ul of methylamine (40% wt. aq. solution) under argon for 18 hours. Chromatography on lipophilic sephadex in MeOH/0.1% TFA followed by silica gel flash (15% MeOH/85% CHCl₃/0.1% TFA) gives 7.9 mg of the desired product.

EXAMPLE 62

7-Amino-6-chloro-1,8-dihydro-5-methyl-8-oxo-pyrrolo[4,3,2-de]quinolinium trifluoroacetate A solution of 10 mg of 7-amino-1-methyl-pyrrolo[4,3,2-de]quinolin-8(1H)-one trifluoroacetate (makaluvamine B) in 5 ml of methyl alcohol is treated with 8.5 mg of N-chlorosuccinimide and stirred overnight. Chromatography on LH-20 lipophilic sephadex gel in methyl alcohol/0.1% TFA followed by silica gel

EXAMPLE 63 AND EXAMPLE 64

7-Amino-6-bromo-1,8-dihydro-5-methyl-8-oxo-pyrrolo[4,3,2-de]quinolinium trifluoroacetate and 7-Amino-2,6-dibromo-1,8-dihydro-5-methyl-8-oxo-pyrrolo[4,3,2-de]quinolinium trifluoroacetate A solution of 20 mg of 7-amino-1-methyl-pyrrolo[4,3,2-de]quinolin-8(1H)-one trifluoroacetate (makaluvamine B) in 5 ml of methyl alcohol is treated with 22.6 mg of N-bromosuccinimide and stirred overnight. Chromatography on LH-20 lipophilic sephadex gel in methyl alcohol/0.1% TFA followed by silica gel flash (15% MeOH/85% CHCl$_3$/0.1% TFA) gives the first product and further chromatography gives the second product.

EXAMPLE 65

7-Amino-1,8-dihydro-6-iodo-5-methyl-8-oxo-pyrrolo[4,3,2-de]quinolinium trifluoroacetate A solution of 10 mg of 7-amino-1-methyl-pyrrolo[4,3,2-de]quinolin-8(1H)-one trifluoroacetate (makaluvamine B) in 5 ml of methyl alcohol is treated with 16 mg of iodine and stirred overnight. Chromatography on LH-20 lipophilic sephadex gel in methyl alcohol/0.1% TFA followed by silica gel flash (15% MeOH/85% CHCl$_3$/0.1% TFA) gives the desired product.

EXAMPLE 66

7-Amino-1,8-dihydro-5-methyl-8-oxo-1-(2-propenyl)-pyrrolo[4,3,2-de]quinolinium trifluoroacetate A solution of 10 mg of 7-amino-1-methyl-8-oxo-pyrrolo[4,3,2-de]quinolin-8 (1H)-one trifluoroacetate (makaluvamine B) in 5 ml of methyl alcohol is combined with 15 ul of allyl iodide and 25 mg of sodium bicarbonate and stirred overnight. Chromatography on LH-20 lipophilic sephadex in methyl alcohol/0.1% TFA followed by silica gel flash (15% MeOH/85% CHCl$_3$/0.1% TFA) gives the desired product.

EXAMPLE 67

7-Amino-1,8-dihydro-5-methyl-1-[(4-nitrophenyl)methyl]-8-oxo-pyrrolo[4,3,2-de]quinolinium trifluoroacetate A solution of 10 mg of 7-amino-1-methyl-8-oxo-pyrrolo[4,3,2-de]quinolin-8(1H)-one trifluoroacetate (makaluvamine B) in 5 ml of methyl alcohol is combined with 27.4 mg of 4-nitrobenzyl bromide and 25 mg of sodium bicarbonate and stirred overnight. Chromatography on LH-20 lipophilic sephadex in methyl alcohol/0.1% TFA followed by silica gel flash (15% MeOH/85% CHCl$_3$/0.1% TFA) gives the desired product.

EXAMPLE 68

7-Amino-1-[(3-chlorophenyl)methyl]-1,8-dihydro-5-methyl-8-oxo-pyrrolo[4,3,2-de]quinolinium trifluoroacetate A solution of 10 mg of 7-amino-1,8-dihydro-1-methyl-8-oxo-pyrrolo[4,3,2-de]quinolin-8(1H)-one trifluoroacetate (makaluvamine B) in 5 ml of methyl alcohol is combined with 26.3 mg of 3-chlorobenzyl bromide and 25 mg of sodium bicarbonate and stirred overnight. Chromatography on LH-20 lipophilic sephadex in methyl alcohol/0.1% TFA followed by silica gel flash (15% MeOH/85% CHCl$_3$/0.1% TFA) gives 10.1 mg of the desired product.

EXAMPLE 69

7-Amino-1,8-dihydro-1-[(3-methoxyphenyl)methyl]-1-methyl-8-oxo-pyrrolo[4,3,2-de]quinolinium trifluoroacetate A solution of 10 mg of 7-amino-1,8-di hydro-1-methyl-8-oxo-pyrrolo[4,3,2-de]quinolin-8(1H)-one trifluoroacetate (makaluvamine B) in 5 ml of methyl alcohol is combined with 19.9 mg of 3-methoxybenzyl bromide and 25 mg of sodium bicarbonate and stirred overnight. Chromatography on LH-20 lipophilic sephadex in methyl alcohol/0.1% TFA followed by silica gel flash (15% MeOH/85% CHCl$_3$/0.1% TFA) gives the desired product.

EXAMPLE 70

7-Amino-1,8-dihydro-5-methyl-8-oxo-1-(phenylmethyl) pyrrolo[4,3,2-de]quinolinium trifluoroacetate A solution of 25 mg of 7-amino-1-methyl-pyrrolo[4,3,2-de]quinolin-8(1H)-one trifluoroacetate (makaluvamine B) in 5 ml of methyl alcohol is combined with 20 ul of benzyl bromide and 100 mg of sodium bicarbonate and stirred overnight. Chromatography on LH-20 lipophilic sephadex in methyl alcohol/0.1% TFA gives the desired product.

EXAMPLE 71

1,8-Dihydro-5-methyl-7-(methylamino)-8-oxo-1-(phenylmethyl)-pyrrolo[4,3,2-de]quinolinium trifluoroacetate A solution of 10 mg of 7-amino-1-methyl-pyrrolo[4,3,2-de]quinolin-8(1H)-one trifluoroacetate (makaluvamine B) in 5 ml of methyl alcohol is combined with 50 ul of methyl iodide and 100 ul of diisopropylethylamine and stirred overnight. Chromatography on LH-20 lipophilic sephadex with methyl alcohol/0.1% TFA gives the desired product.

EXAMPLE 72 AND EXAMPLE 73

1,8-Dihydro-1-(3-methoxy-3-oxopropyl)-7-[7-[(3-methoxy-3-oxopropyl]amino]-5-methyl-8-oxo-pyrrolo[4,3,2-de]quinolinium trifluoroacetate and 7-Amino-1,8,dihydro-1-(3-methoxy-3-oxopropyl)5-methyl-8-oxo-pyrrolo[4,3,2-de]quinolinium trifluoroacetate A solution of 25 mg of 7-amino-1-methyl-8-oxo-pyrrolo[4,3,2-de]quinolin-8(1H)-one trifluoroacetate (makaluvamine B) in 5 ml of methyl alcohol is combined with 250 ul of diisopropylethylamine and 250 ul of methyl acrylate and stirred overnight. Chromatography on LH-20 lipophilic sephadex in methyl alcohol/0.1% TFA followed by silica gel flash (15% MeOH/85% CHCl$_3$/0.1% TFA) gives the first product and further elution gives the second product.

EXAMPLE 74 AND EXAMPLE 75

7-Amino-1,8-dihydro-1,5-dimethyl-8-oxo-pyrrolo[4,3,2-de]quinolinium trifluoroacetate and 1,8-Dihydro, 1,5-dimethyl-7-(methylamino)-8-oxo-pyrrolo[4,3,2-de]-quinolinium trifluoroacetate A solution of 76.4 mg of 7-amino-1-methyl-8-oxo-pyrrolo[4,3,2-de]quinolin-8(1H)-one trifluoroacetate (makaluvamine B) in 5 ml of methyl alcohol is combined with 100 ul of methyl iodide and 25 mg of sodium bicarbonate and stirred overnight. Chromatography on LH-20 lipophilic sephadex in methyl alcohol/0.1% TFA followed by silica gel flash (15% MeOH/85% CHCl$_3$/0.1% TFA) gives the first product and further elution gives the second product.

EXAMPLE 76

7-Amino-1,8-dihydro-1-methyl-8-oxo-5-(2-propenyl)[4,3,2-de]quinolinium trifluoroacetate A solution of 10 mg of 7-amino-1-methyl-pyrrolo[4,3,2-de]quinolin-8(1H)-one trifluoroacetate (makaluvamine B) in 5 ml of methyl alcohol is combined with 15 ul of allyl iodide and 25 mg of sodium bicarbonate and stirred overnight. Chromatography on LH-20 lipophilic sephadex in methyl alcohol/0.1% TFA followed by silica gel flash (15% MeOH/85% CHCl$_3$/0.1% TFA) gives the desired product.

EXAMPLE 77 AND EXAMPLE 78

7-Amino-1,8-dihydro-1-methyl-8-oxo-5,6-bis (Phenylmethyl-pyrrolo-[4,3,2-de]quinolinium trifluoroacetate and 1,8-Dihydro-1-methyl-8-oxo-5-(phenylmethyl)-7-[(phenylmethyl)amino]pyrrolo[4,3,2-de]quinolinium trifluoroacetate A solution of 25 mg of 7-amino-1-methyl-pyrrolo[4,3,2-de]quinolin-8(1H)-one trifluoroacetate (makaluvamine B) in 10 ml of methyl alcohol is combined with 100 ul of benzyl bromide and 50 mg of sodium bicarbonate and stirred overnight. Chromatography on LH-20 lipophilic sephadex in methyl alcohol/0.1% TFA followed by silica gel flash (15% MeOH/85% CHCl$_3$/0.1% TFA) gives the first desired product and further elution gives the second desired product.

EXAMPLE 79

1,3,4,8-Tetrahydro-5-methyl-7(methyl-d-amino)-8-oxo-pyrrolo[4,3,2-de]quinolinium trifluoroacetate A solution of 10 mg of 7-amino-1,8-1-methyl-oxo-pyrrolo[4,3,2-de]quinolin-8(1H)-one trifluoroacetate (makaluvamine B) in 1 ml of degassed methyl alcohol is stirred for two hours under nitrogen with rigorous exclusion of oxygen. This mixture is then treated with 20 mg of NaBD$_4$ followed by treatment with 13 ul of formaldehyde. Chromatography on LH-20 lipophilic sephadex in methyl alcohol/0.1% TFA followed by silica gel flash (15% MeOH/85% CHCl$_3$/0.1% TFA) gives the desired product.

EXAMPLE 80

1,8-dihydro-7[(3-methoxy-3-oxopropyl)amino]-5-methyl-8-oxo-pyrrolo[4,3,2-de]quinolinium trifluoroacetate A solution of 10 mg of 7-amino-1-methyl-pyrrolo[4,3,2-de]quinolin-8(1H)-one trifluoroacetate (makaluvamine B) in 1 ml of degassed methyl alcohol is stirred for two hours under nitrogen with rigorous exclusion of oxygen. This mixture is then treated with 5 mg of NaBH$_4$ followed by treatment with 100 ul of methyl acrylate. Chromatography on LH-20 lipophilic sephadex in methyl alcohol/0.1% TFA followed by silica gel flash (15% MeOH/85% CHCl$_3$/0.1% TFA) gives the desired product.

EXAMPLE 81 AND EXAMPLE 82

1,8-Dihydro-5-methyl-7-(octylamino)-8-oxo-pyrrolo[4,3,2-de]quinolinium trifluoroacetate and 1,8-Dihydro-5-methyl-7-(dioctylamino)-8-oxo-pyrrolo[4,3,2-de.]quinolinium trifluoroacetate A solution of 10 mg of 7-amino-1-methyl-pyrrolo[4,3,2-de]quinolin-8(1H)-one trifluoroacetate (makaluvamine B) in 1 ml of degassed methyl alcohol is stirred for two hours under nitrogen with rigorous exclusion of oxygen. This mixture is then treated with 5 mg of NaBH$_4$ followed by treatment with 50 ul of octyl aldehyde. Chromatography on LH-20 lipophilic sephadex in methyl alcohol/0.1% TFA followed by silica gel flash (15% MeOH/85% CHCl$_3$/0.1% TFA) gives the first desired product and further elution gives the second desired product.

EXAMPLE 83

1,8-Dihydro-5-methyl-7-[(2-methylethyl)amino]-8-oxo-pyrrolo[4,3,2-de]quinolinium trifluoroacetate A solution of 10 mg of 7-amino-1-methyl-pyrrolo[4,3,2-de]quinolin-8(1H)-one trifluoroacetate (makaluvamine B) in 1 ml of degassed methyl alcohol is stirred for two hours under nitrogen with rigorous exclusion of oxygen. This mixture is then treated with 5 mg of NaBH$_4$ followed by treatment with 25 ul of acetone. Chromatography on LH-20 lipophilic sephadex in methyl alcohol/0.1% TFA followed by silica gel flash (15% MeOH/85% CHCl$_3$/0.1% TFA) gives the desired product.

EXAMPLE 84

7-(Cyclohexylamino)-1,8-dihydro-5-methyl-8-oxo-pyrrolo[4,3,2-.de]quinolinium trifluoroacetate A solution of 10 mg of 7-amino-1-methyl-pyrrolo[4,3,2-de]quinolin-8(1H)-one trifluoroacetate (makaluvamine B) in 1 ml of degassed methyl alcohol is stirred for two hours under nitrogen with rigorous exclusion of oxygen. This mixture is then treated with 5 mg of NaBH$_4$ followed by treatment with 30 ul of cyclohexanone. Chromatography on LH-20 lipophilic sephadex in methyl alcohol/0.1% TFA followed by silica gel flash (15% MeOH/85% CHCl$_3$/0.1% TFA) gives the desired product.

EXAMPLE 85

7-(Dimethylamino)-1,8..dihydro-5-methyl-8-oxo-pyrrolo[4,3,2-de]quinolinium trifluoroacetate A solution of 10 mg of 7-amino-1-methyl-pyrrolo[4,3,2-de]quinolin-8(1H)-one trifluoroacetate (makaluvamine B) in 1 ml of degassed methyl alcohol is stirred for two hours under nitrogen with rigorous exclusion of oxygen. This mixture is then treated with 5 mg of NaBH₄ followed by treatment with 25 ul of 40% w/v formaldehyde. Chromatography on LH-20 lipophilic sephadex in methyl alcohol/0.1% TFA followed by silica gel flash (15% MeOH/85% CHCl₃/0.1% TFA) gives the desired product.

EXAMPLE 86

7-[(3-Furanylmethyl)amino]-1,8-dihydro-5-methyl-8-oxo-pyrrolo[4,3,2-de]quinolinium trifluoroacetate A solution of 10 mg of 7-amino-1-methyl-pyrrolo[4,3,2-de]quinolin-8 (1H)-one trifluoroacetate (makaluvamine B) in 1 ml of degassed methyl alcohol is stirred for two hours under nitrogen with rogorous exclusion of oxygen. This mixture is then treated with 5 mg of NaBH₄ followed by treatment with 25 ul of 2-furaldehyde. Chromatography on LH-20 lipophilic sephadex in methyl alcohol/0.1% TFA followed by silica gel flash (15% MeOH/85% CHCl₃/0.1% TFA) gives the desired product.

EXAMPLE 87

1,8-Dihydro-5-methyl-7-[(1-naphthalenylmethyl-)amino]-8-oxo-pyrrolo[4,3,2-de]quinolinium trifluoroacetate A solution of 10 mg of 7-amino-1-methyl-pyrrolo[4,3,2-de]quinolin-8(1H)-one trifluoroacetate (makaluvamine B) in 1 ml of degassed methyl alcohol is stirred for two hours under nitrogen with rigorous exclusion of oxygen. This mixture is then treated with 5 mg of NaBH₄ followed by treatment with 34 ul of 1-naphthaldehyde. Chromatography on LH-20 lipophilic sephadex in methyl alcohol/0.1% TFA followed by silica gel flash (15% MeOH/85% CHCl₃/0.1% TFA) gives desired product.

EXAMPLE 88

7-[[(4-Carboxylphenyl)methyl]amino]-1,8-dihydro-5-methyl-8-oxo-pyrrolo[4,3,2-de]quinolinium trifluoroacetate A solution of 10 mg of 7-amino-1-methyl-pyrrolo[4,3,2-de]quinolin-8(1H)-one trifluoroacetate (makaluvamine B) in 1 ml of degassed methyl alcohol is stirred for two hours under nitrogen with rigorous exclusion of oxygen. This mixture is then treated with 5 mg of NaBH₄ followed by treatment with 50 mg of carboxybenzaldehyde. Chromatography on LH-20 lipophilic sephadex in methyl alcohol/0.1% TFA followed by silica gel flash (15% MeOH/85% CHCl₃/0.1% TFA) gives the first product.

EXAMPLE 89

1,8-Dihydro-5-methyl-8-oxo-7-[(phenylmethyl)amino]-pyrrolo[4,3,2-de]quinolinium trifluoroacetate A solution of 10 mg of 7-amino-1-methyl-pyrrolo[4,3,2-de]quinolin-8(1H)-one trifluoroacetate (makaluvamine B) in 1 ml of degassed methyl alcohol is stirred for two hours under nitrogen with rigorous exclusion of oxygen. This mixture is then treated with 5 mg of NaBH₄ followed by treatment with 50 ul of benzyl bromide. Chromatography on LH-20 lipophilic sephadex in methyl alcohol/0.1% TFA followed by silica gel flash (15% MeOH/85% CHCl₃/0.1% TFA) gives the desired product.

EXAMPLE 90

1,8-Dihydro-7-[[[4-hydroxy-3-methoxyphenyl)methyl-]amino]-5-methyl-8-oxo-pyrrolo[4,3,2-de]quinolin-8(1H)-one trifluoroacetate A solution of 10 mg of 7-amino-1-methyl-pyrrolo[4,3,2-de]quinolin-8(1H)-one trifluoroacetate (makaluvamine B) in 1 ml of degassed methyl alcohol is stirred for two hours under nitrogen with rigorous exclusion of oxygen. This mixture is then treated with 5 mg of NaBH₄ followed by treatment with 50 mg of 4-methoxy-3-hydroxybenzaldehyde. Chromatography on LH-20 lipophilic sephadex in methyl alcohol/0.1% TFA followed by silica gel flash (15% MeOH/85% CHCl₃/0.1% TFA) gives the desired product.

EXAMPLE 91

1,8-Dihydro-7-[[(4-methoxyphenyl)methyl]amino]-5-methyl-8-oxo-pyrrolo[4,3,2-de]quinolinium trifluoroacetate A solution of 10 mg of 7-amino-1-methyl-pyrrolo[4,3,2-de]quinolin-8 (1H)-one trifluoroacetate (makaluvamine B) in 1 ml of degassed methyl alcohol is stirred for two hours under nitrogen with rigorous exclusion of oxygen. This mixture is then treated with 5 mg of NaBH₄ followed by treatment with 40 ul of 4methoxybenzaldehyde. Chromatography on LH-20 lipophilic sephadex in methyl alcohol/0.1% TFA followed by silica gel flash (15% MeOH/85% CHCl₃/0.1% TFA) gives the desired product.

EXAMPLE 92

1,8-Dihydro-7-[[(4-hydroxyphenyl)methyl]amino]5-methyl-8-oxo-pyrrolo[4,3,2-de]quinolin-8(1H)-one trifluoroacetate A solution of 10 mg of 7-amino-1-methyl-pyrrolo[4,3,2-de]quinolin-8(1H)-one trifluoroacetate (makaluvamine B) in 1 ml of degassed methyl alcohol is stirred for two hours under nitrogen with rigorous exclusion of oxygen. This mixture is then treated with 5 mg of NaBH₄ followed by treatment with 50 mg of 4hydroxybenzaldehyde. Chromatography on LH-20 lipophilic sephadex in methyl alcohol/0.1% TFA followed by silica gel flash (15% MeOH/85% CHCl₃/0.1% TFA) gives the desired product.

EXAMPLE 93

7-[[[4-(Dimethylamino)phenyl]methyl]amino]-1,8-dihydro-5-methyl-8-oxo-pyrrolo[4,3,2-de]quinolinium trifluoroacetate A solution of 10 mg of 7-amino-1-methyl-pyrrolo[4,3,2-de]quinolin-8(1H)-one trifluoroacetate (makaluvamine B) in 1 ml of degassed methyl alcohol is stirred for two hours under nitrogen with rigorous exclusion of oxygen. This mixture is then treated with 5 mg of NaBH₄ followed by treatment with 50 mg of 4-(dimethylamino)benzaldehyde. Chromatography on LH-20 lipophilic sephadex in methyl alcohol/0.1% TFA followed by silica gel flash (15% MeOH/85% CHCl₃/0.1% TFA) gives the desired product.

EXAMPLE 94 AND EXAMPLE 95

3,5,6,7-Tetrahydro-1,8,9-trimethyl-6-oxo-2M-dipyrrolo[4,3,2-de:2',3'-h]quinolinium and trifluoroacetate and 7,7'-[(1.2-dimethyl-1,2-ethanediyl)diimino]bis[1,3,4,8-tetrahydro-5-methyl-8-oxo-pyrrolo[4,3,2-de]quinolinium trifluoroacetate A solution of 10 mg of 7-amino-1-methyl-pyrrolo[4,3,2-de]quinolin-8(1H)-one trifluoroacetate (makaluvamine B) in 15 ml of degassed methyl alcohol is stirred for two hours under nitrogen with rigorous exclusion of oxygen. This mixture is treated with 25 mg of NaBH$_4$ followed by treatment with 100 ul of 2,3-butanedione. Chromatography on LH-20 lipophilic sephadex in methyl alcohol/0.1% TFA followed by silica gel flash (15% MeOH/85% CHCl$_3$/0.1% TFA) gives the first desired product. Further elution gives the second desired product as a mixture of a pair of enantiomeric compounds and a meso compound.

EXAMPLE 96

7-Amino-1-(2-cyanoethyl)-1,8-dihydro-5-methyl-8-oxo-pyrrolo[4,3,2-de]quinolinium trifluoroacetate A solution of 10 mg of 7-amino-1-methyl-pyrrolo[4,3,2-de]quinolin-8(1H)-one trifluoroacetate is dissolved in 1 ml of methyl alcohol and combined with 5 mg of potassium carbonate and 50 ul of acrylonitrile and stirred overnight. Chromatography on LH-20 lipophilic sephadex in methyl alcohol/0.1% TFA followed by silica gel flash (15% MeOH/85% CHCl$_3$/0.1% TFA) gives the desired product.

EXAMPLE 97

7,7'-(1,4-Dimethyl-1,4-butanediyldiimino)-bis-[1,8-dihydro-5-methyl-8-oxo-pyrrolo[4,3,2-[de]quinolinium trifluoroacetate A solution of 10 mg of 7-amino-1-methyl-pyrrolo[4,3,2-de]quinolin-8(1H)-one trifluoroacetate (malaluvamine B) in 1 ml of degassed methyl alcohol is stirred for two hours under nitrogen with rigorous exclusion of oxygen. This mixture is treated with 5 mg of NaBH$_4$ followed by treatment with 37 ul of acetonylacetone. Chromatography on LH-20 lipophilic sephadex in methyl alcohol/0.1% TFA followed by silica gel flash (15% MeOH/85% CHCl$_3$/0.1% TFA) gives the desired product as a mixture of a pair of enantiomeric compounds and a meso compound.

EXAMPLE 98

1,8-Dihydro-7-[(2-hydroxy-2-phenylethyl)amino]-5-methyl-8-oxo-pyrrolo[4,3,2-de]quinolinium trifluoroacetate A solution of 10 mg of 7-amino-1-methyl-pyrrolo[4,3,2-de]quinolin-8(1H)-one trifluoroacetate (malaluvamine B) in 1 ml of degassed methyl alcohol is stirred for two hours under nitrogen with rigorous exclusion of oxygen. This mixture is then treated with 4 mg of NaBH$_4$ followed by treatment with 48 mg of phenylglyoxal monohydrate. Chromatography on LH-20 lipophilic sephadex in methyl alcohol/0.1% TFA followed by silica gel flash (15% MeOH/85% CHCl$_2$/0.1% TFA) gives the desired product.

EXAMPLE 99

1,8-Dihydro-5-methyl-7-[(2-phenylethenyl)amino]-8-oxo-pyrrolo[4,3,2-de]quinolinium trifluoroacetate A solution of 5 mg 1,8-dihydro-7-[(2-hydroxy-2-phenylethyl)-amino]-5-methyl-8-oxo-pyrrolo[4,3,2-de]quinolinium trifluoroacetate (Example 98) in 1 ml of pyridine is treated with 100 ul of trifluoroacetic anhydride. Chromatography on LH-20 lipophilic sephadex in methyl alcohol/0.1% TFA gives the desired product.

Utility

The performance of the novel compounds of the present invention are shown in the following in vitro test. The results of this test for representative compounds of the invention are shown in Table II.

Experimental Design and Methods

I. In vitro tumor panel evaluation

The cytotoxic activity of the pyrrolo[4,3,2-de]quinolin-8(1H)-ones against a panel of >20 human tumor cell lines is determined using the Sulforhodamine B protein dye-binding colorimetric cytotoxicity assay (SRB) described by Skehan et al. (Journal National Cancer Institute 82:1107–1112, 1990), as modified by Monks et al., (Journal National Cancer Institute 83: 757–766, 1991). In this assay, $1 \times 10^4$ cells are plated in each well of a 96-well microtitre plate, and after 24 hours, the test compounds are added to the cells in duplicate over a five-log range (0.01–100 ug/ml, final concentration) in a diluent that contains no greater than 1% dimethylsulfoxide (DMSO). Positive controls (i.e., etoposide) are included in every experiment. Treatments are for 48 hours, after which cells are fixed in 10% trichloroacetic acid (10% final concentration), washed five times with deionized water and stained with SRB solution (0.4% in glacial acetic acid). Protein-bound stain is solubilized with 0.1 ml tris buffer and the adsorbance values are recorded with a microplate reader. Duplicate plates of cells are fixed with trichloroacetic acid at the time of drug addition to establish To values, as described by Monks et al. (JNCl, 83: 757–766, 1991). The effect of drug treatments over the five-long range of concentrations is calculated using the formula, T—To/C—To, to determine the IC$_{50}$ values.

The results of the in vitro cell panel evaluation are summarized in Table II. The pyrrolo[4,3,2-de]quinolin-8(1H)-ones are compared to the cancer drug etoposide because they share a similar mechanism of action against Topoismerase II (see results presented in Table II). The results described in Table II are described as follows:

1) IC$_{50}$ values are reported as ug/ml, with AVG IC$_{50}$ referred to the Mean IC$_{50}$ value for all 20 cell lines. Several of the pyrroloiminoquinones (e.g., Example Nos. 6 and 38) were 1-log more potent than the reference topoisomerase inhibitor, etoposide, and 23/33 of these compounds had AVG IC$_{50}$ values less than etoposide (i.e., they were more potent).

2) MIN IC$_{50}$ represents the IC$_{50}$ value of the most sensitive cell line, and MAX IC$_{50}$, the IC$_{50}$ value of the least sensitive cell line. Five of the test compounds had MIN IC$_{50}$ values less than etoposide, and 16/33 had MAX IC$_{50}$ values that were less than etoposide.

3) The ratio values for DDP/S; CaCo2/CX1; MIP/SW620, and; HCT15/SKBR3 refer to the IC$_{50}$ value for resistant cell lines included in the tumor cell panel, divided by the $IC_{50}$ value for corresponding drug sensitive cell lines. For example, DDP is a Cisplatin resistant ovarian carcinoma cell line, and S is the corresponding parent drug sensitive ovarian carcinoma cell line (A2780). As shown in Table II, DDP is cross resistant to etoposide and has an $IC_{50}$ value that is 53-fold higher than the parent cell line. In constrast to etoposide, the pyrrolo[4,3,2-de]quinolin-8(1H)-ones are generally not cross resistant in this cisplatin resistant cell line. CaCo2 is a slow growing non P-glycoprotein multidrug resistant colon carcinoma cell line. MIP is a colon carcinoma cell line that expresses P-glycoprotein and is multidrug resistant; SW620 is a drug sensitive colon carcinoma cell line. HCT15 is a colon carcinoma cell line that is resistant to topoisomerase inhibitors and SKBR3 is a breast carcinoma that is very sensitive to topoisomerase inhibitors. HCT15 is 22-fold more resistant to etoposide than SKBR3.

As can be seen from Table II, the compounds demonstrate excellent cytotoxic activity.

II. In vivo antitumor activity

Compounds with demonstrated activity in the diverse cell base cancer screen are initially tested for antitumor activity against two sensitive tumor models. 1) The Ovcar3 human ovarian carcinoma grown as a subcutaneous solid tumor in Balb/C nu/nu athymic (i.e., nude) mice, and 2) the P388 murine leukemia grown as an ascites tumor in conventional immune competent mice. Antitumor activity in the solid tumor model is assessed by comparing the size of the treated tumors (T) to that of control tumors (C) over a 3-4 week period and calculating the minimum T/C×100% (i.e., the smallest size the tumor obtained in the treated animals relative to the control, the smaller the number the more active the compound). Activity in the murine ascites tumor model is calculated as % Increase in Median Life Span (%ILS) compared to control animals (i.e., the higher the number, the more active the compound). All compounds are initially tested at three different dose levels on a day 1, 5, 9 schedule (day one after P388 i.p. innoculation; day one after staging for the Ovcar 3 solid tumor). Compounds are administered by i.p. injection in Klucell vehicle. Results are reported at the maximum non-lethal dose. Compared to the two approved anticancer drugs used in this evaluation (i.e., vincristin and etoposide). The results are presented in Table III. As can be seen from Table III, the compounds demonstrate excellent cytotoxic activity.

TABLE II

| | IN-VITRO TUMOR PANEL EVALUATION | | | | | | |
|---|---|---|---|---|---|---|---|
| | IC50 | | | | | | |
| EXAMPLE # | AVG | MIN | MAX | DDP/S | CaCO2/CX1 | MIP/SW620 | HCT15/SKBR3 |
| 1 | 1 | 0.36 | 2.17 | | 0.3 | 1.1 | 1.9 |
| 2 | 18 | 2.03 | 25.1 | 1.0 | 0.6 | 0.9 | 6.7 |
| 3 | 1.7 | 0.06 | 10 | | 0.3 | 1.1 | 1.9 |
| 5 | 2.3 | 1.23 | 3.44 | 1.1 | 1.5 | 1.1 | 0.3 |
| 6 | 0.4 | 0.11 | 1.45 | 1.8 | 6.3 | 5.1 | 3.5 |
| 9 | 37 | 23 | 50 | 1.4 | | | |
| 10 | 5.1 | 1.29 | 10 | | 0.25 | 0.7 | 1.5 |
| 13 | 2.4 | 0.4 | 7.71 | 1.1 | 0.7 | 0.9 | 1.7 |
| 14 | 2.3 | 0.84 | 3.54 | 1.2 | 0.8 | 1.4 | 2.1 |
| 21 | 1.4 | 0.28 | 4.47 | 1.5 | 0.8 | 7.0 | 7.1 |
| 23 | 2.1 | 0.45 | 4.2 | 1.2 | 1.0 | 8.6 | 3.8 |
| 25 | 13 | 1.32 | 50 | 6.1 | 7.3 | | 23.5 |
| 27 | 15 | 0.17 | 50 | 5.1 | 15.1 | | 288.0 |
| 29 | 2.6 | 1.03 | 5.7 | | 2.9 | 1.8 | 1.8 |
| 30 | 4.5 | 0.41 | 25.9 | 1.1 | 3.6 | 65.8 | 12.7 |
| 31 | 1.7 | 0.34 | 2.59 | 1.2 | 0.6 | 8.0 | 2.7 |
| 32 | 2.1 | 0.37 | 10 | | 1.8 | 0.9 | 3.5 |
| 35 | 5.7 | 1.2 | 24.4 | 1.0 | 1.3 | 20.3 | 9.1 |
| 39 | 0.8 | 0.19 | 2.71 | 1.7 | 4.8 | 9.0 | 122.0 |
| 40 | 5.8 | 0.25 | 50 | 1.3 | 8.3 | | 102.0 |
| 41 | 6.5 | 0.05 | 50 | 1.8 | 8.3 | | 737.0 |
| 43 | 6.4 | 0.27 | 36.3 | 1.6 | 19.8 | 90.8 | 78.5 |
| 44 | 5.6 | 0.02 | 27.1 | 11.3 | 32.0 | 67.8 | 1140.0 |
| 45 | 33 | 8.99 | 50 | 1.2 | | 1.2 | 1.6 |
| 46 | 7 | 0.2 | 22.3 | 1.6 | 5.4 | 8.3 | 113.0 |
| 48 | 7.7 | 0.02 | 50 | 11.0 | 38.0 | | 2090.0 |
| 49 | 3.3 | 0.92 | 13.9 | 1.1 | 1.0 | 4.2 | 15.4 |
| 51 | 48 | 35.6 | 50 | | | | |
| 52 | 25 | 12.3 | 50 | 1.1 | 0.8 | 1.5 | 2.6 |
| 54 | 18 | 2.26 | 50 | 1.2 | 4.2 | | 3.9 |
| 56 | 4.7 | 1.56 | 21.5 | 1.0 | 1.4 | 2.0 | 3.1 |
| 57 | 13 | 0.43 | 50 | 1.8 | 100.8 | | 32.1 |
| 58 | 11 | 0.22 | 50 | 1.5 | 34.0 | 167.0 | 227.0 |
| ETOPOSIDE | 8.7 | 0.12 | 27.9 | 53.0 | 4.2 | 1.9 | 22.3 |

DDP/S - CIS-PLATIN RESISTANCE
CACO2/CX1 - GROWTH KINETICS
MIP101/SW620 - MDR(p-glycoprotein) RESISTANCE
HCT15/SKBR3 - TOPOISOMERASE RESISTANCE

TABLE III

In Vivo Antitumor Activity of Representative pyrrolo[4,3,2-de]quinolin-8(1H)-ones

| Compound | Dose mg/kg | Ovcar3 Min T/C % | P388 ILS % |
|---|---|---|---|
| Vincristine | 0.8 | 53% | >91%* |
| Etoposide | 8.0 | 62% | ND |
| Example #1 | 5.0 | 94% | 9% |
| Example #3 | 5.0 | 37%* | 18% |

*Significant at P > 0.05, Student's T-Test.

Antibacterial and BIA Activity of the pyrrolo[4,3,2-de]quinolin-8(1H)-ones

The antibacterial activity of the pyrrolo[4,3,2-de]quinolin-8(1H)-ones is assessed against a panel of Gram-positive and Gram-negative microorganisms. One hundred fifty milliliters of agar medium are seeded with 1 ml of diluted culture and aseptically poured into 9 inch×9 inch Nunc bioassay plates. The twenty-five microliters of the test sample dissolved in DMSO are placed in 5.5 mm wells that are cut into agar layer which has been pre-seeded with the test bacterial strains. The plates are incubated at 37° C. for 18–24 hours. Zones of inhibition are recorded.

Each of the compounds is tested in the Biochemical Induction Assay (Elespuru, R. and Yarmolinsky, M., Environmental mutagensis, 1, 65–78, 1979), a test to specifically measure the ability of an agent to directly or indirectly initiate DNA damage.

invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, poly-

TABLE IV

Antibacterial activity of the pyrrolo[4,3,2-de]quinolin-8(1H)-ones
ANTIBACTERIAL ACTIVITY OF THE MAKALUVAMINE COMPOUNDS
ASSAY ORGANISMS

| COMPOUND NUMBER | [CONC] microgram/ml | B. subtilis 17 | B. subtilis rec+ 307 | B. subtilis rec E4 308 | S. aureus 375 | S. aureus meth r 310 | S. aureus cipro r 400 | E. faecium 379 | E. coli 300 | K. pneumoniae 53 | C. freundii 395 | BIA BR513 |
|---|---|---|---|---|---|---|---|---|---|---|---|---|
| | | | | ZONES OF INHIBITION (MM) | | | | | | | | |
| 1 | 1000 | 11 | 13 | 13H | | | | | 16 | 17H | 14 | 10T |
| | 250 | | 8 | 9H | | | | | 10H | 13H | 10H | 8T |
| | 64 | | | | | | | | | | | |
| 3 | 1000 | | | | | | | | | | | 8T |
| | 250 | | | | | | | | | | | |
| | 64 | | | | | | | | | | | |
| 6 | 1000 | 16 | 11 | 13 | 10:14H | 10 | 11:14H | 12H | 12 | | | 8T |
| | 250 | 15 | 10 | 8:10H | 7H | 9 | 9:13H | 11H | 11 | | | |
| | 64 | 12:14H | 9H | 10H | | 8 | 11H | 9H | 9 | | | |
| CINODINE CONTROL | 1000 | 13 | | | 9 | 7 | | | 9 | 14:17H | 8H | |
| | 250 | 11 | | | 7 | | | | | 12 | | |
| | 64 | 8 | | | | | | | | 10 | | |
| | 16 | | | | | | | | | 8 | | |
| BLEOMYCIN CONTROL | 3.7 | | | | | | | | | | | 3+ T |
| | 1.8 | | | | | | | | | | | 2+ T |
| | 0.9 | | | | | | | | | | | 1+ T |

H = HAZY ZONES
T = TOXIC
ALL SAMPLES IN 20% DMSO
AGAR DIFFUSION ASSAY 25 microliter sample in 5.5 mm well As can be seen from Table IV, the compounds demonstrate excellent antibacterial activity.

When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the ethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

We claim:

1. An essentially pure compound of the formula I, II or III

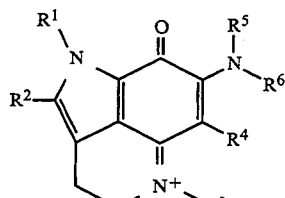

Formula I

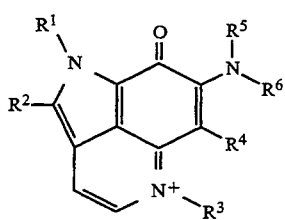

Formula II or

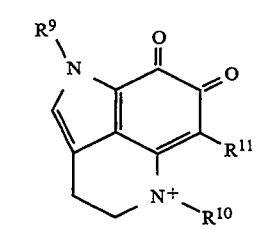

Formula III wherein:

$R^1$ is H, straight alkyl of 1 to 4 carbon atoms, allyl, benzyl optionally substituted with straight alkyl of 1 to 4 carbon atoms, trifluoromethyl, nitro, O-alkyl of 1 to 4 carbon atoms straight chain, —$NR^7R^7$, F, Cl, Br,

or -$CO_2R^9$), benzyl disubstituted with straight alkyl of 1 to 4 carbon atoms, trifluoromethyl, nitro, O-alkyl of 1 to 4 carbon atoms straight chain, —$NR^7R^7$, F, Cl, Br, OH,

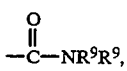

—$CO_2R^9$), with the proviso that $R^4$ is not Cl in Formula II;

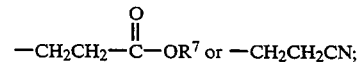

$R^2$ is H, Cl, Br or I;

$R^3$ is H, straight alkyl of 1 to 4 carbon atoms, benzyl, monosubstituted benzyl substituted with straight alkyl of 1 to 4 carbon atoms, trifluoromethyl, nitro, or O-alkyl of 1 to 4 carbon atoms straight chain, —$NR^7R^7$, F, Cl, Br, OH,

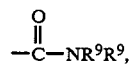

or —$CO_2R^9$, disubstituted benzyl substituted with straight alkyl of 1 to 4 carbon atoms, trifluoromethyl, nitro, O-alkyl of 1 to 4 carbon atoms straight chain, —$NR^7R^7$, F,Cl, Br, OH,

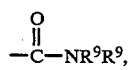

or —$CO_2R^9$;

$R^4$ is H, straight alkyl of 1 to 4 carbon atoms, Cl, Br, I, benzyl, mono-substituted benzyl substituted with straight alkyl of 1 to 4 carbon atoms, trifluoromethyl, nitro, O-alkyl of 1 to 4 carbon atoms straight chain, —$NR^7R^7$, F, Cl, Br, OH,

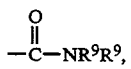

—$CO_2R^9$, disubstituted benyl substituted with straight alkyl of 1 to 4 carbon atoms, trifluoromethyl, nitro, O-alkyl of 1 to 4 carbon atoms straight chain, —$NR^7R^7$, F, Cl, Br, OH,

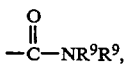

or —$CO_2R^9$; with the proviso that $R_4$ is not Cl in Formula II;

$R^5$ is H, straight or branched alkyl of 1 to 10 carbon atoms,

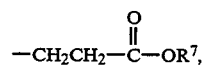

—$CH_2R^8$, benzyl optionally substituted with straight alkyl of 1 to 4 carbon atoms, trifluoromethyl, nitro, O-alkyl of 1 to 4 carbon atoms, straight chain, hydroxyl, —$NR^7R^7$, F, Cl, Br,

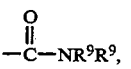

or —$CO_2R^9$, disubstituted benzyl substituted with straight alkyl of 1 to 4 carbon atoms, trifluoromethyl, nitro, O-alkyl of 1 to 4 carbon atoms straight chain, hydroxyl, —$NR^7R^7$, F, Cl, Br,

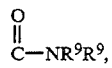

or —CO$_2$R$^9$—CH$_2$—furan, —CH$_2$-thiophene, —CH$_2$-naphthyl, —CH$_2$-pyridyl

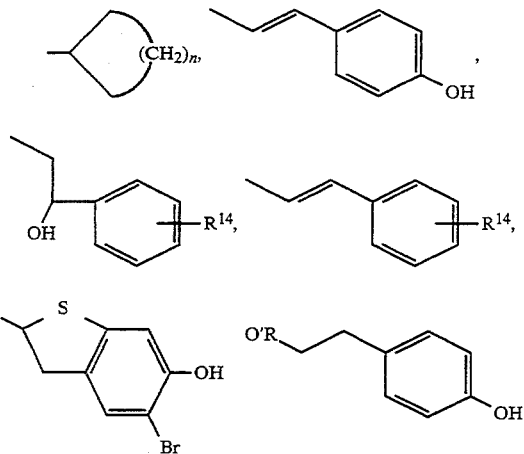

phenyl substituted with straight alkyl of 1 to 4 carbon atoms, trifluoromethyl, nitro, O-alkyl of 1 to 4 carbon atoms straight chain, hydroxyl, F, Cl, or Br, disubstituted phenyl substituted with straight alkyl of 1 to 4 carbon atoms, trifluoromethyl, nitro, O-alkyl of 1 to 4 carbon atoms straight chain, hydroxyl, F, Cl or Br[)];

n is 2 to 5;
R$^6$ is H, or CH$_2$R$^8$;
R$^7$ is straight alkyl 1 to 4 carbon atoms;
R$^8$ is straight alkyl 1 to 7 ,carbon atoms;
R$^9$ is H or straight alkyl 1 to 4 carbon atoms;
R$^{10}$ is H or straight alkyl 1 to 4 carbon atoms;
R$^{11}$ is H or Br and R$^{14}$ is F, Cl, Br., NO$_2$, straight alkyl of 1 to 4 carbon atoms, O-alkyl of 1 to 4 carbon atoms straight chain or trifluoromethyl; or pharmaceutically acceptable salts thereof.

2. An essentially pure compound according to claim 1 of the formula:

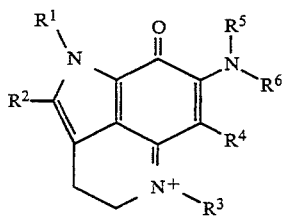

wherein:
R$^1$ is H, straight alkyl of 1 to 4 carbon atoms, allyl, benzyl optionally substituted with straight alkyl of 1 to 4 carbon atoms, trifluoromethyl, nitro, O-alkyl of 1 to 4 carbon atoms straight chain, —NR$^7$R$^7$, F, Cl, Br,

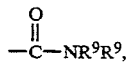

or —CO$_2$R$^9$, disubstituted benzyl substituted with straight alkyl of 1 to 4 carbon atoms, trifluoromethyl, nitro, O-alkyl of 1 to 4 carbon atoms straight chain, —NR$^7$R$^7$, F, Cl, Br, OH,

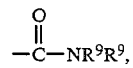

—CH$_2$CH$_2$—C—OR$^7$ or —CH$_2$CH$_2$CN;

R$^2$ is H, Cl, Br or I;
R$^3$ is H, straight alkyl of 1 to 4 carbon atoms, benzyl optionally substituted with straight alkyl of 1 to 4 carbon atoms, trifluoromethyl, nitro, or O-alkyl of 1 to 4 carbon atoms straight chain, —NR$^7$R$^7$, F, Cl, Br OH,

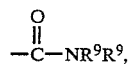

or —CO$_2$R$^9$, disubstituted benzyl substituted with straight alkyl of 1 to 4 carbon atoms, trifluoromethyl, nitro, O-alkyl of 1 to 4 carbon atoms straight chain, —NR$^7$R$^7$, F, Cl, Br, OH,

or —CO$_2$R$^9$;
R$^4$ is H, straight alkyl of 1 to 4 carbon atoms, Cl, Br, I, benzyl optionally substituted with straight alkyl of 1 to 4 carbon atoms, trifluoromethyl, nitro, O-alkyl of 1 to 4 carbon atoms straight chain, —NR$^7$R$^7$, F, Cl, Br, OH,

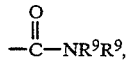

or —CO$_2$R$^9$, disubstituted benzyl substituted with straight alkyl of 1 to 4 carbon atoms, trifluoromethyl, nitro, O-alkyl of 1 to 4 carbon atoms straight chain, —NR$^7$R$^7$, F, Cl, Br, OH,

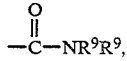

or —CO$_2$R$^9$;
R$^5$ is H, straight or branched alkyl of 1 to 10 carbon atoms,

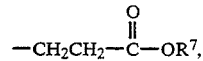

—CH$_2$R$^8$, optionally substituted with straight alkyl of 1 to 4 carbon atoms, trifluoromethyl, nitro, O-alkyl of 1 to 4 carbon atoms, straight chain, hydroxyl, —NR$^7$R$^7$, F, Cl, Br

or —CO$_2$R$^9$), disubstituted benzyl substituted with straight alkyl of 1 to 4 carbon atoms, trifluoromethyl, nitro, O-alkyl of 1 to 4 carbon atoms straight chain, hydroxyl, —NR$^7$R$^7$, F, Cl, Br,

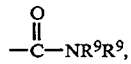

or —CO$_2$R$^9$, —CH$_2$- furan, —CH$_2$- thiophene, —CH$_2$-naphthyl, —CH$_2$-pyridyl

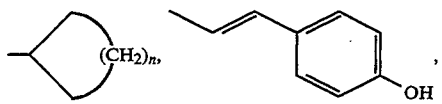

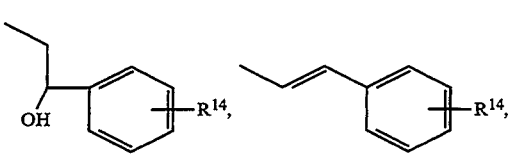

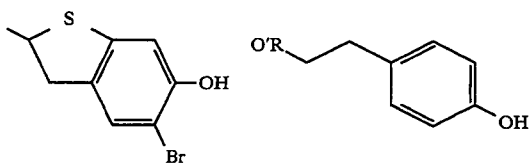

phenyl optionally substituted with straight alkyl of 1 to 4 carbon atoms, trifluoromethyl, nitro, O-alkyl of 1 to 4 carbon atoms straight chain, hydroxyl, F, Cl, or Br, disubstituted phenyl substituted with straight alkyl of 1 to 4 carbon atoms, trifluoromethyl, nitro, O-alkyl of 1 to 4 carbon atoms straight chain, hydroxyl, F, Cl, or Br;

n is 2 to 5;
R$^6$ is H, or CH$_2$R$^8$;
R$^7$ is straight alkyl 1 to 4 carbon atoms;
R$^8$ is straight alkyl 1 to 7 carbon atoms;
R$^9$ is H or straight alkyl 1 to 4 carbon atoms; or pharmaceutically acceptable salts thereof.

3. An essentially pure compound according to claim 1 of the formula:

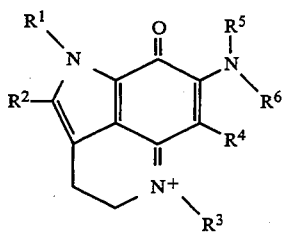

wherein:
R$^1$ is H or straight alkyl of 1 to 4 carbon atoms;
R$^2$ is H;
R$^3$ is H or straight alkyl of 1 to 4 carbon atoms;
R$^4$ is H;
R$^5$ is H,

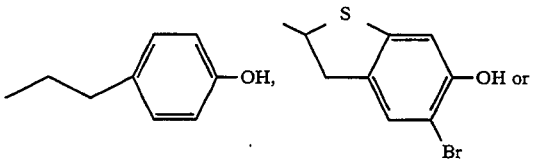

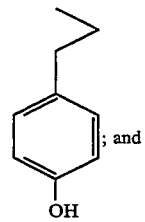

and
R$^6$ is H.

4. The essentially pure compound according to claim 3  7-amino-1,3,4,8-tetrahydro-5-methyl-8-oxo-pyrrolo[4,3,2-de]quinolinium trifluoroacetate (makaluvamine C)

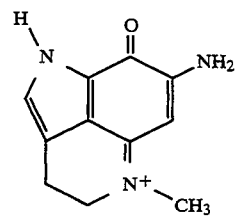

5. The essentially pure compound according to claim 3  7-[[2-(4-hydroxyphenyl)ethyl]amino]-3,4-dihydro-pyrrolo[4,3,2-de]quinolin-8(1H)-one trifluoroacetate (makaluvamine D)

6. The essentially pure compound according to claim 3 (E)-7-[[2-(4-hydroxyphenyl)ethenyl]amino]-1-methyl-3,4-dihydro-pyrrolo[4,3,2-de]quinolin-8(1H)-one trifluoroacetate (makaluvamine E)

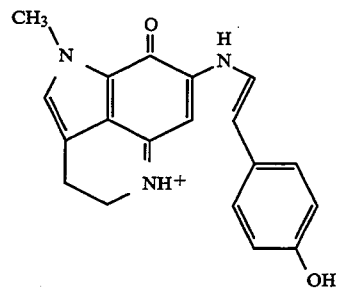

7. The essentially pure compound according to claim 3 7-amino(5-bromo-2,3-dihydro-6-hydroxybenzo[b]thien-2-yl)-3,4-dihydro-pyrrolo[4,3,2-de]quinolin-8(1H)-one trifluoroacetate (makaluvamine F)

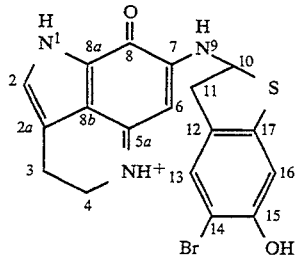

8. A compound according to claim 1 of the formula:

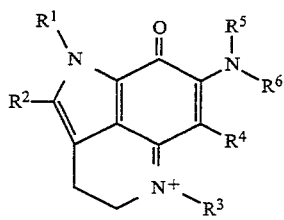

wherein:

$R^1$ is H, straight alkyl of 1 to 4 carbon atoms, allyl, benzyl optionally substituted with straight alkyl of 1 to 4 carbon atoms, trifluoromethyl, nitro, O-alkyl of 1 to 4 carbon atoms straight chain, $-NR^7R^7$, F, Cl, Br,

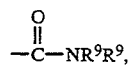

or $-CO_2R^9$, disubstituted benzyl substituted with straight alkyl of 1 to 4 carbon atoms, trifluoromethyl, nitro, O-alkyl of 1 to 4 carbon atoms straight chain, $-NR^7R^7$, F, Cl, Br, OH,

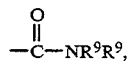

or $-CO_2R^9$,

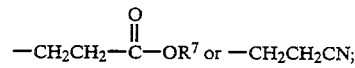

$R^2$ is H, Cl, Br or I;
$R^3$ is H, straight alkyl of 1 to 4 carbon atoms, benzyl optionally substituted with straight alkyl of 1 to 4 carbon atoms, trifluoromethyl, nitro, or O-alkyl of 1 to 4 carbon atoms straight chain, $-NR^7R^7$, F, Cl, Br, OH,

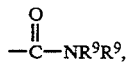

or $-CO_2R^9$, disubstituted benzyl substituted with straight alkyl of 1 to 4 carbon atoms, trifluoromethyl, nitro, O-alkyl of 1 to 4 carbon atoms straight chain, $-NR^7R^7$, F, Cl, Br, OH,

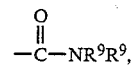

or $-CO_2R^9$, $R^4$ is H, straight alkyl of 1 to 4 carbon atoms, Cl, Br, I, benzyl optionally substituted with straight alkyl of 1 to 4 carbon atoms, trifluoromethyl, nitro, O-alkyl of 1 to 4 carbon atoms straight chain., $-NR^7R^7$, F, Cl, Br, OH,

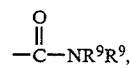

or $-CO_2R^9$, disubstituted benzyl substituted with straight alkyl of 1 to 4 carbon atoms, trifluoromethyl, nitro, O-alkyl of 1 to 4 carbon atoms straight chain, $-NR^7R^7$, F, Cl, Br, OH,

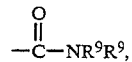

or $-CO_2R^9$,
$R^5$ is H, straight or branched alkyl of 1 to 10 carbon atoms,

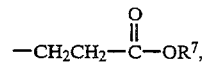

$-CH_2R^8$, benzyl optionally substituted with straight alkyl of 1 to 4 carbon atoms, trifluoromethyl, nitro, O-alkyl of 1 to 4 carbon atoms, straight chain, hydroxyl, $-NR^7R^7$, F, Cl, Br

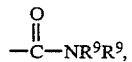

or $-CO_2R^9$, disubstituted benzyl substituted with straight alkyl of 1 to 4 carbon atoms, trifluoromethyl, nitro, O-alkyl of 1 to 4 carbon atoms straight chain, hydroxyl, $-NR^7R^7$, F, Cl, Br,

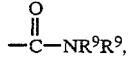

or $CO_2R$, $-CH_2$-furan, $-CH_2$-thiophene, $-CH_2$-naphthyl, $-CH_2$-pyridyl

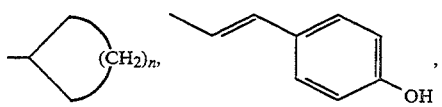

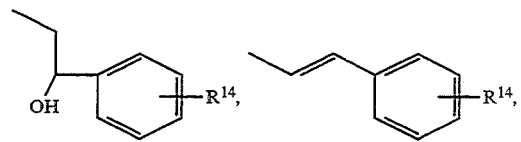

phenyl optionally substituted with straight alkyl of 1 to 4 carbon atoms, trifluoromethyl, nitro, O-alkyl of 1 to 4 carbon atoms straight chain, hydroxyl, F, Cl, or Br, disubstituted phenyl substituted with straight alkyl of 1 to 4 carbon atoms, trifluoromethyl, nitro, O-alkyl of 1 to 4 carbon atoms straight chain, hydroxyl, F, Cl, or Br;

n is 2 to 5;

$R^6$ is H, or $CH_2R^8$;

$R^7$ is straight alkyl 1 to 4 carbon atoms;

$R^8$ is straight alkyl 1 to 7 carbon atoms;

$R^9$ is H or straight alkyl 1 to 4 carbon atoms; and pharmaceutically acceptable salts; with the provisos that $R^1$ cannot be methyl when $R^2$, $R^3$, $R^4$, $R^5$ and $R^6$ are hydrogen; $R^1$, $R^2$ $R^4$, $R^5$ and $R^6$ cannot be hydrogen when $R^3$ is methyl; $R^1$, $R^2$, $R^3$, $R^4$ and $R^6$ cannot be H when $R^5$ is $R^1$ cannot be methyl when $R^2$, $R^3$, $R^4$ and $R^6$ are hydrogen and $R^5$ is $R^1$, $R^2$, $R^3$, $R^4$ and $R^5$ cannot be hydrogen when $R^6$ is 9. An essentially pure compound according to claim 1 of the formula:

wherein:

$R^1$ is H, straight alkyl of 1 to 4 carbon atoms, allyl, benzyl optionally substituted with straight alkyl of 1 to 4 carbon atoms, trifluoromethyl, nitro, O-alkyl of 1 to 4 carbon atoms straight chain, —NR⁷R⁷, F, Cl, Br, $$-\overset{O}{\underset{\|}{C}}-NR^9R^9,$$

or —CO₂R⁹, disubstituted benzyl substituted with straight alkyl of 1 to 4 carbon atoms, trifluoromethyl, nitro, O-alkyl of 1 to 4 carbon atoms straight chain, —NR⁷R⁷, F, Cl, Br, OH, $$-\overset{O}{\underset{\|}{C}}-NR^9R^9,$$

or —CO₂R⁹, $$-CH_2CH_2-\overset{O}{\underset{\|}{C}}-OR^7 \text{ or } -CH_2CH_2CN;$$

$R^2$ is H, Cl, Br or I;

$R^3$ is H, straight alkyl of 1 to 4 carbon atoms, benzyl substituted with straight alkyl of 1 to 4 carbon atoms, trifluoromethyl, nitro, or O-alkyl of 1 to 4 carbon atoms straight chain, —NR⁷R⁷, F, Cl, Br, OH, $$-\overset{O}{\underset{\|}{C}}-NR^9R^9,$$

or —CO₂R⁹, disubstituted benzyl substituted with straight alkyl of 1 to 4 carbon atoms, trifluoromethyl, nitro, O-alkyl of 1 to 4 carbon atoms straight chain, —NR⁷R⁷, F, Cl, Br, OH, $$-\overset{O}{\underset{\|}{C}}-NR^9R^9,$$

or —CO₂R⁹;

$R^4$ is H, straight alkyl of 1 to 4 carbon atoms, Cl, Br, I, benzyl optionally substituted with straight alkyl of 1 to 4 carbon atoms, trifluoromethyl, nitro, O-alkyl of 1 to 4 carbon atoms straight chain, —NR⁷R⁷, F, Cl, Br, OH, $$-\overset{O}{\underset{\|}{C}}-NR^9R^9,$$

or —CO₂R⁹, disubstituted benzyl substituted with straight alkyl of 1 to 4 carbon atoms, trifluoromethyl, nitro, O-alkyl of 1 to 4 carbon atoms, straight chain, —NR⁷R⁷, F, Cl, Br, OH, $$-\overset{O}{\underset{\|}{C}}-NR^9R^9,$$

or —CO₂R⁹;

$R^5$ is H, straight or branched alkyl of 1 to 10 carbon atoms, $$-CH_2CH_2-\overset{O}{\underset{\|}{C}}-OR^7,$$

—CH$_2$R$^8$, benzyl optionally substituted with straight alkyl of 1 to 4 carbon atoms, trifluoromethyl, nitro, O-alkyl of 1 to 4 carbon atoms, straight chain, hydroxyl, —NR$^7$R$^7$, F, Cl, Br

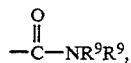

or —CO$_2$R$^9$, disubstituted benzyl substituted with straight alkyl of 1 to 4 carbon atoms, trifluoromethyl, nitro, O-alkyl of 1 to 4 carbon atoms straight chain, hydroxyl, —NR$^7$R$^7$, F, Cl, Br,

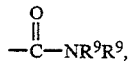

or —CO$_2$R$^9$, —CH$_2$-furan, —CH$_2$-thiophene —CH$_2$-naphthyl —CH$_2$-pyridyl

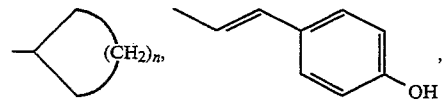

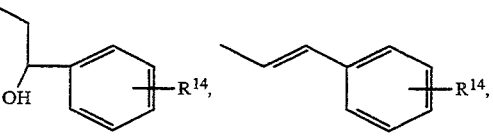

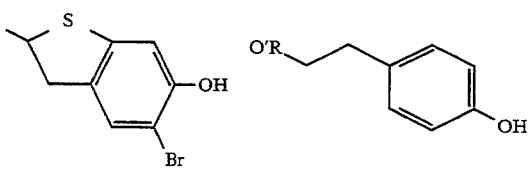

phenyl optionally substituted with straight alkyl of 1 to 4 carbon atoms, trifluoromethyl, nitro, O-alkyl of 1 to 4 carbon atoms straight chain, hydroxyl, F, Cl, or Br, disubstituted phenyl substituted with straight alkyl of 1 to 4 carbon atoms, trifluoromethyl, nitro, O-alkyl of 1 to 4 carbon atoms straight chain, hydroxyl, F, Cl, or Br;

n is 2 to 5;

R$^6$ is H, or CH$_2$R$^8$;

R$^7$ is straight alkyl 1 to 4 carbon atoms;

R$^8$ is straight alkyl 1 to 7 carbon atoms;

R$^9$ is H or straight alkyl 1 to 4 carbon atoms; or pharmaceutically acceptable salts thereof.

10. A compound according to claim 9 of the formula:

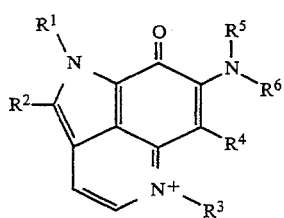

wherein:

R$^1$ is H, straight alkyl of 1 to 4 carbon atoms, allyl, benzyl optionally substituted with straight alkyl of 1 to 4 carbon atoms, trifluoromethyl, nitro, O-alkyl of 1 to 4 carbon atoms straight chain, —NR$^7$R$^7$, F, Cl, Br,

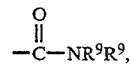

or —CO$_2$R$^9$, disubstituted, benzyl substituted with straight alkyl of 1 to 4 carbon atoms, trifluoromethyl, nitro, O-alkyl of 1 to 4 carbon atoms straight chain, —NR$^7$R$^7$, F, Cl, Br, OH,

or —CO$_2$R$^9$,

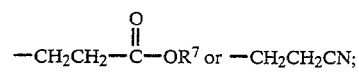

R$^2$ is H, Cl, Br or I;

R$^3$ is H, straight alkyl of 1 to 4 carbon atoms, benzyl optionally substituted with straight alkyl of 1 to 4 carbon atoms, trifluoromethyl, nitro, or O-alkyl of 1 to 4 carbon atoms straight chain, —NR$^7$R$^7$, F, Cl, Br, OH,

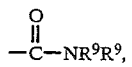

or —CO$_2$R$^9$, disubstituted benzyl substituted with straight alkyl of 1 to 4 carbon atoms, trifluoromethyl, nitro, O-alkyl of 1 to 4 carbon atoms straight chain, —NR$^7$R$^7$, F, Cl, Br, OH,

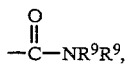

or —CO$_2$R$^9$,

R$^4$ is H, straight alkyl of 1 to 4 carbon atoms, Cl, Br, I, benzyl optionally substituted with straight alkyl of 1 to 4 carbon atoms, trifluoromethyl, nitro, O-alkyl of 1 to 4 carbon atoms straight chain, —NR$^7$R$^7$, F, Cl, Br, OH,

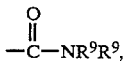

or —CO$_2$R$^9$, disubstituted benzyl substituted with straight alkyl of 1 to 4 carbon atoms, trifluoromethyl, nitro, O-alkyl of 1 to 4 carbon atoms straight chain, —NR$^7$R$^7$, F, Cl, Br, OH,

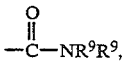

or —CO$_2$R$^9$,

R$^5$ is H, straight or branched alkyl of 1 to 10 carbon atoms,

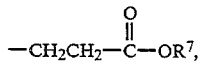

—CH₂R⁸ benzyl optionally substituted with straight alkyl of 1 to 4 carbon atoms, trifluoromethyl, nitro, O-alkyl of 1 to 4 carbon atoms, straight chain, hydroxyl, —NR⁷R⁷, F, Cl, Br

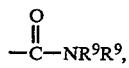

or —CO₂R⁹, disubstituted benzyl substituted with straight alkyl of 1 to 4 carbon atoms, trifluoromethyl, nitro, O-alkyl of 1 to 4 carbon atoms straight chain, hydroxyl, —NR⁷R⁷, F, Cl, Br,

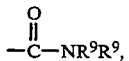

or —CO₂R⁹, CH₂-furan, —CH₂ thiophene —CH₂-naphthyl, —CH₂-pyridyl

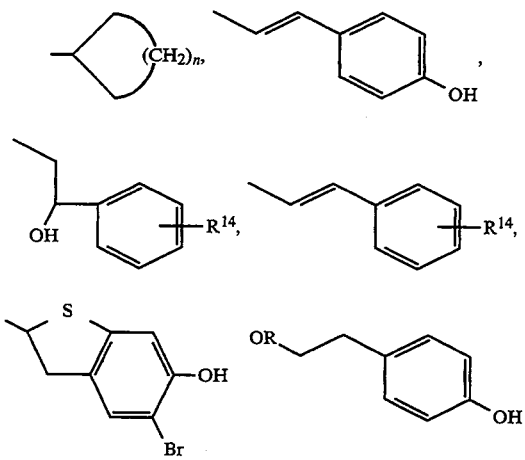

phenyl optionally substituted with straight alkyl of 1 to 4 carbon atoms, trifluoromethyl, nitro, O-alkyl of 1 to 4 carbon atoms straight chain, hydroxyl, F, Cl, or Br, disubstituted phenyl substituted with straight alkyl of 1 to 4 carbon atoms, trifluoromethyl, nitro, O-alkyl of 1 to 4 carbon atoms straight chain, hydroxyl, F, Cl, or Br; n is 2 to 5;
R⁶ is H, or CH₂R⁸;
R⁷ is straight alkyl 1 to 4 carbon atoms;
R⁸ is straight alkyl 1 to 7 carbon atoms;
R⁹ is H or straight alkyl 1 to 4 carbon atoms; or pharmaceutically acceptable salts thereof; with the proviso that R¹ cannot be methyl when R², R³, R⁴, R⁵ and R⁶ are H.

11. An essentially pure compound according to claim 1 of the formula:

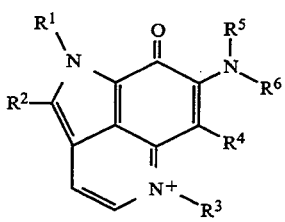

wherein:
R¹ is straight alkyl of 1 to 4 carbon atoms;
R², R³, R⁴, R⁵ and R⁶ are H or pharmaceutically acceptable salts thereof.

12. The essentially pure compound according to claim 11 7-amino-1-methyl-pyrrolo[4,3,2-de]quinolin-8(1H)-one trifluoroacetate (makaluvamine B)

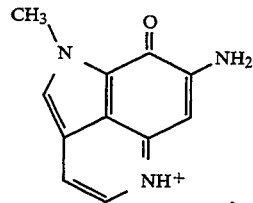

13. A compound according to claim 1 of the formula:

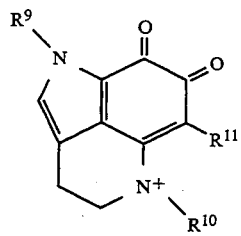

wherein:
R⁹ is H or straight alkyl 1 to 4 carbon atoms;
R¹⁰ is H or straight alkyl 1 to 4 carbon atoms;
R¹¹ is H or Br;
with the proviso that R⁹ and R¹¹ cannot be H when R¹⁰ is methyl or pharmaceutically acceptable salts thereof.

14. The compound according to claim 13 1,3,4,5-tetrahydro-1,5-dimethyl-pyrrolo[4,3,2-de]quinoline-7,8-dione trifluoroacetate.

15. The compound according to claim 13 1,3,4,5-tetrahydro-5-methyl-pyrrolo-[4,3,2-de]quinoline-7,8-dione trifluoroacetate.

16. The compound according to claim 13 7-amino-1-(2-cyanoethyl)-1,3,4,8-tetrahydro-5-methyl-8-oxo-pyrrolo[4,3,2-de]quinolinium trifluoroacetate.

17. The compound according to claim 13 1,3,4,8-tetrahydro-7-[(2-hydroxy-2-phenylethyl)-amino]-5-methyl-8-oxo-pyrrolo- [4,3,2-de]quinolinium trifluoroacetate.

18. The compound according to claim 13 1,3,4,8-tetrahydro-5-methyl-7-[(2-phenylethenyl)amino]-8-oxopyrrolo- [4,3,2-de]quinolinium trifluoroacetate.

19. The compound according to claim 1 7-amino-6-chloro-1,3,4,8-tetrahydro-5-methyl-8-oxo-pyrrolo[4,3,2-de]quinolinium trifluoroacetate.

20. The compound according to claim 1 7-amino-6-chloro-3,4-dihydro-1-methyl-8-oxo-pyrrolo[4,3,2-de]-quinolin-8(1H)-one trifluoroacetate.

21. The compound according to claim 1 7-amino-6-bromo-1,3,4,8-tetrahydro-5-methyl-8-oxo-pyrrolo[4,3,2-de]quinolinium trifluoroacetate.

22. The compound according to claim 1 7-amino-2,6-dibromo-1,3,4,8-tetrahydro-5-methyl-8-oxo-pyrrolo[4,3,2-de]quinolinium trifluoroacetate.

23. The compound according to claim 1 7-amino-6-bromo-3,4-dihydro-1-methyl-8-oxo-pyrrolo[4,3,2-de]-quinolin-8(1H)-one trifluoroacetate.

24. The compound according to claim 1 7-amino-2,6-dibromo-3,4-dihydro-1-methyl-pyrrolo[4,3,2-de]quinolin-8(1H)-one trifluoroacetate.

25. The compound according to claim 1 7-amino-1,3,4,8-tetrahydro-6-iodo-5-methyl-8-oxo-pyrrolo[4,3,2-de]quinolinium trifluoroacetate.

26. The compound according to claim 1 7-amino-1,3,4,8-tetrahydro-5-methyl-8-oxo-1-(2-propenyl)-pyrrolo[4,3,2-de]quinolinium trifluoroacetate.

27. The compound according to claim 1 7-amino-1,3.4,8-tetrahydro-5-methyl-1-[(4-nitrophenyl)methyl]-8-oxo-pyrrolo[4,3,2-de]quinolinium trifluoroacetate.

28. The compound according to claim 1 7-amino-1-[(3-chlorophenyl)methyl]-1,3,4,8-tetrahydro- 5-methyl-8-oxo-pyrrolo[4,3,2-de]quinolinium trifluoroacetate.

29. The compound according to claim 1 7-amino-1,3,4,8-tetrahydro-1-[(3-methoxyphenyl)methyl]-5-methyl-8-oxo-pyrrolo[4,3,2-de]quinolinium trifluoroacetate.

30. The compound according to claim 1 7-amino-1,3,4,8-tetrahydro-5-methyl-8-oxo-1-(phenylmethyl)-pyrrolo[4,3,2-de]quinolinium trifluoroacetate.

31. The compound according to claim 1 1,3,4,8-tetrahydro-7-[(3-methoxy-3-oxopropyl)amino]-5-methyl-8-oxo-1-(phenylmethyl)pyrrolo[4,3,2-de]quinolinium trifluoroacetate.

32. The compound according to claim 1 1,3,4,8-tetrahydro-5-methyl-7-(methylamino)-8-oxo-1-(phenylmethyl)-pyrrolo[4,3,2-de]quinolinium trifluoroacetate.

33. The compound according to claim 1 1,3,4,8-tetrahydro-1-(3-methoxy-3-oxopropyl)-7-[7-[(3-methoxy-3-oxopropyl)amino]-5-methyl-8-oxo-pyrrolo[4,3,2-de]quinolinium trifluoroacetate.

34. The compound according to claim 1 7-amino-1,3,4,8-tetrahydro-1-(3-methoxy-3-oxopropyl)-5-methyl-8-oxo-pyrrolo[4,3,2-de]quinolinium trifluoroacetate.

35. The compound according to claim 1 7-amino-1,3,4,8-tetrahydro-1,5-dimethyl-8-oxo-pyrrolo[4,3,2-de]quinolinium trifluoroacetate.

36. The compound according to claim 1 1,3,4,8-tetrahydro-1,5-dimethyl-7-(methylamino)-8-oxo-pyrrolo[4,3,2-de]quinolinium trifluoroacetate.

37. The compound according to claim 1 7-amino-1,3,4,8-tetrahydro-1-methyl-8-oxo-5-(2-propenyl)[4,3,2-de]quinolinium trifluoroacetate.

38. The compound according to claim 1 7-amino-1,3,4,8-tetrahydro-1-methyl-8-oxo-5-(phenylmethyl)-pyrrolo[4,3,2-de]quinolinium trifluoroacetate.

39. The compound according to claim 1 7-amino-1,3,4,8-tetrahydro-1-methyl-8-oxo-5,6-bis(phenylmethyl-pyrrolo-[4,3,2-de]quinolinium trifluoroacetate.

40. The compound according to claim 1 1,3,4,8-tetrahydro-1-methyl-8-oxo-5-(phenylmethyl)-7-[(phenylmethyl)amino]pyrrolo[4,3,2-de]quinolinium trifluoroacetate.

41. The compound according to claim 1 1,3,4,8-tetrahydro-5-methyl-7-(methylamino)-8-oxo-pyrrolo[4,3,2-de]quinolinium trifluoroacetate.

42. The compound according to claim 1 1,3,4,8-tetrahydro-5-methyl-7(methyl-d-amino)-8-oxo-pyrrolo[4,3,2-de]quinolinium trifluoroacetate.

43. The compound according to claim 1 1,3,4,8-tetrahydro-7[(3-methoxy-3-oxopropyl)amino]-5-methyl-8-oxo-pyrrolo[4,3,2-de]quinolinium trifluoroacetate.

44. The compound according to claim 1 1,3,4,8-tetrahydro-5-methyl-7-(octylamino)-8-oxo-pyrrolo[4,3,2-de]quinolinium trifluoroacetate.

45. The compound according to claim 1 1,3,4,8-tetrahydro-5-methyl-7-(dioctylamino)-8-oxo-pyrrolo[4,3,2-de]quinolinium trifluoroacetate.

46. The compound according to claim 1 1,3,4,8-tetrahydro-5-methyl-7-[(2-methylethyl)amino]-8-oxo-pyrrolo[4,3,2-de]quinolinium trifluoroacetate.

47. The compound according to claim 1 7-(cyclohexylamino)-1,3,4,8-tetrahydro-5-methyl-8-oxo-pyrrolo[4,3,2-de]quinolinium trifluoroacetate.

48. The compound according to claim 1 7-(dimethylamino)-1,3,4,8-tetrahydro-5-methyl-8-oxo-pyrrolo[4,3,2-de]quinolinium trifluoroacetate.

49. The compound according to claim 1 7-[(3-furanylmethyl)amino]-1,3,4,8-tetrahydro-5-methyl-8-oxo-pyrrolo[4,3,2-de]quinolinium trifluoroacetate.

50. The compound according to claim 1 1,3,4,8-tetrahydro-5-methyl-7-[(1-naphthalenylmethyl)amino]-8-oxo-pyrrolo[4,3,2-de]quinolinium trifluoroacetate.

51. The compound according to claim 1 7-[[(4-carboxylphenyl)methyl]amino]-1,3,4,8-tetrahydro-5-methyl-8-oxo-pyrrolo[4,3,2-de]quinolinium trifluoroacetate.

52. The compound according to claim 1 1,3,4,8-tetrahydro-5-methyl-8-oxo-7-[(phenylmethyl)amino]-pyrrolo[4,3,2-de]quinolinium trifluoroacetate.

53. The compound according to claim 1 1,3,4,8-tetrahydro-7-[[(4-hydroxy-3-methoxyphenyl)methyl]amino]-5-methyl-8-oxo-pyrrolo[4,3,2-de]quinolin-8(1H)-one trifluoroacetate.

54. The compound according to claim 1 1,3,4,8-tetrahydro-7-[[(4-methoxyphenyl)methyl]amino]-5-methyl-8-oxo-pyrrolo[4,3,2-de]quinolinium trifluoroacetate.

55. The compound according to claim 1 1,3,4,8-tetrahydro-7-[[(4-hydroxyphenyl)methyl]amino]-5-methyl-8-oxo-pyrrolo[4,3,2-de]quinolin-8(1H)-one trifluoroacetate.

56. The compound according to claim 1 7-[[[4-(dimethylamino)phenyl]methyl]amino]-1,3,4,8-tetrahydro-5-methyl-8-oxo-pyrrolo[4,3,2-de]quinolinium trifluoroacetate.

57. The compound according to claim 1 1,3,4,5-tetrahydro-1-methyl-pyrrolo[4,3,2-de]-quinoline-7,8-dione trifluoroacetate.

58. The essentially pure compound 6-bromo-1,3,4,5-tetrahydro-1-methyl-pyrrolo[4,3,2-de]quinoline-7,8-dione trifluoroacetate (makaluvone)

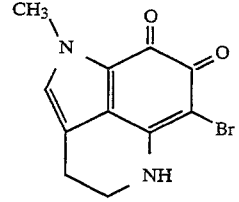

59. The compound 7,7'-[(1,2-dimethyl-1,2-ethanediyl)diimino]bis-[1,3,4,8-tetrahydro-5-methyl-8-oxo-pyrrolo[4,3,2-de]-quinolinium trifluoroacetate.

60. The compound 7,7'-(1,4-dimethyl-1,4-butanediyl-diimino)-bis-[1,3,4,8-tetrahydro-5-methyl-8-oxo-pyrrolo[4,3,2-de]quinolinium trifluoroacetate.

61. A pharmaceutical composition useful for treatment or control of neoplastic disease in a mammal comprising a suitable pharmaceutical carrier and a compound of claim 1.

62. A method for treatment or control of neoplastic disease of the ovary or colon in a mammal comprising administering a compound of claim 1 to said mammal in an amount effective to treat or control the neoplastic disease.

63. A method according to claim 62 wherein the compound is 7-amino-1,3,4,8-tetrahydro-5-methyl-8-oxo-pyrrolo[4,3,2-de]quinolinium trifluoroacetate.

64. A method according to claim 62 wherein the compound is 7-(5-bromo-2,3-dihydro-6-hydroxybenzo-[b]-thien-2-yl)-3,4-dihydro-pyrrolo-[4,3,2-de]quinolin-8(1H)-one trifluoroacetate.

65. A method according to claim 62 wherein the compound is 7-amino-1-[(3-chlorophenyl)methyl]-1,3,4,8-tetrahydro-5-methyl-8-oxo-pyrrolo[4,3,2-de]-quinolinium trifluoroacetate.

66. A method according to claim 62 wherein the compound is 1,3,4,8-tetrahydro-5-methyl-7-(dioctylamino)-8-oxo-pyrrolo[4,3,2-de]quinolinium trifluoroacetate.

67. A method according to claim 62 wherein the compound is 1,3,4,8-tetrahydro-5-methyl-7-[(1-naphthalenyl methyl)amino]-8-oxo-pyrrolo[4,3,2-de]-quinolinium trifluoroacetate.

68. A method according to claim 62 wherein the compound is 1,3,4,8-tetrahydro-7-[[(4-methoxyphenyl)-methyl]-amino]-5-methyl-8-oxo-pyrrolo[4,3,2-de]-quinolinium trifluoroacetate.

69. A method according to claim 62 wherein the compound is 1,3,4,8-tetrahydro-7-[[(4-hydroxyphenyl)-methyl]amino]-5-methyl-8-oxo-pyrrolo[4,3,2-de]quinolin-8(1H)-one trifluoroacetate.

70. A compound of the formula:

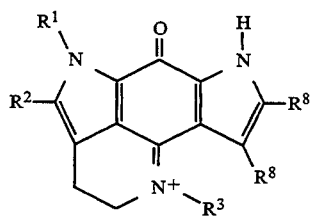

wherein $R^1$ is H, straight alkyl of 1 to 4 carbon atoms, allyl, benzyl optionally substituted with straight alkyl of 1 to 4 carbon atoms, trifluoromethyl, nitro, O-alkyl of 1 to 4 carbon atoms straight chain, —$NR^7R^7$, F, Cl, Br,

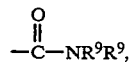

or —$CO_2R^9$, disubstituted benzyl substituted with straight alkyl of 1 to 4 carbon atoms, trifluoromethyl, nitro, O-alkyl of 1 to 4 carbon atoms straight chain, —$NR^7R^7$, F, Cl, Br, OH,

or —$CO_2R^9$,

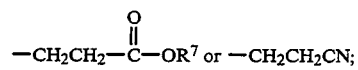

$R^2$ is H, Cl, Br or I;

$R^3$ is H, straight alkyl of 1 to 4 carbon atoms, benzyl substituted with straight alkyl of 1 to 4 carbon atoms, trifluoromethyl, nitro, or O-alkyl of 1 to 4 carbon atoms straight chain, —$NR^7R^7$, F, Cl, Br, OH,

or —$CO_2R^9$, disubstituted benzyl substituted with straight alkyl of 1 to 4 carbon atoms, trifluoromethyl, nitro, O-alkyl of 1 to 4 carbon atoms straight chain, —$NR^7R^7$, F, Cl, Br, OH,

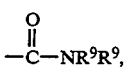

or —$CO_2R^9$;

$R^7$ is straight alkyl of 1 to 4 carbon atoms;

$R^9$ is H or straight alkyl of 1 to 4 carbon atoms;

$R^8$ is straight alkyl of 1 to 7 carbon atoms, phenyl optionally substituted with straight alkyl of 1 to 4 carbon atoms, trifluoromethyl, nitro, O-alkyl of 1 to 4 carbon atoms straight chain, hydroxyl, F, Cl, or Br, disubstituted phenyl substituted with straight alkyl of 1 to 4 carbon atoms, trifluoromethyl, nitro, O-alkyl of 1 to 4 carbon atoms straight chain, hydroxyl, F, Cl or Br, benzyl or indole or pharmaceutically acceptable salts thereof.

71. The compound according to claim 70, 3,5,6,7-tetrahydro-1,8,9-trimethyl-6-oxo-2H-dipyrrolo[4,3,2-de:2',3'-h]quinolinium trifluoroacetate.

* * * * *